United States Patent [19]
Van Ooijen et al.

[11] Patent Number: 6,022,846
[45] Date of Patent: *Feb. 8, 2000

[54] EXPRESSION OF PHYTASE IN PLANTS

[75] Inventors: Albert J. J. Van Ooijen, Voorburg; Krun Rietveld, Vlaardingen; Andreas Hoekema, Oegstgeest; Jan Pen, Leiden; Peter Christian Sijmons, Amsterdam; Teunis Cornelis Verwoerd, Leiden, all of Netherlands

[73] Assignee: Mogen International and Gist-brocades N.V., Netherlands

[ * ] Notice: This patent is subject to a terminal disclaimer.

[21] Appl. No.: 09/097,847

[22] Filed: Jun. 15, 1998

Related U.S. Application Data

[63] Continuation-in-part of application No. 08/693,709, Aug. 7, 1996, Pat. No. 5,770,413, which is a continuation-in-part of application No. 08/146,424, Nov. 2, 1993, Pat. No. 5,593,963, which is a continuation-in-part of application No. 07/756,864, Sep. 11, 1991, abandoned, which is a continuation-in-part of application No. 07/586,765, Sep. 21, 1990, abandoned.

[30] Foreign Application Priority Data

Mar. 25, 1991 [EP] European Pat. Off. .............. 91200687

[51] Int. Cl.[7] ................. C11B 9/00; C12N 5/04; C12N 15/82; A01H 5/00
[52] U.S. Cl. ................. 512/5; 426/630; 435/172.1; 435/172.3; 435/375; 435/196; 800/278; 800/290; 800/298
[58] Field of Search .................. 426/630; 435/172.1, 435/172.3, 375, 196; 800/278, 290, 298; 512/5

[56] References Cited

PUBLICATIONS

Napoli et al. Plant Cell. 1989. vol. 2: 278–289.
Matzke and Matzke. 1995. vol. 107: 679–685.
Gellatly et al. Plant Physiol. 1990 (suppplement). vol. 93: abstract 562.
Shimamoto et al. Nature. 1989. vol. 338: 274–276.

*Primary Examiner*—Lynette R. F. Smith
*Assistant Examiner*—Ousama Zaghmout
*Attorney, Agent, or Firm*—Morrison & Foerster LLP

[57] ABSTRACT

The present invention provides for the expression of phytase in transgenic plants or plant organs and methods for the production of such plants. DNA expression constructs are provided for the transformation of plants with a gene encoding phytase under the control of regulatory sequences which are capable of directing the expression of phytase. These regulatory sequences include sequences capable of directing transcription in plants, either constitutively, or stage and/or tissue specific, depending on the use of the plant or parts thereof. The transgenic plants and plant organs provided by the present invention may be applied to a variety of industrial processes either directly, e.g. in animal feeds or alternatively, the expressed phytase may be extracted and if desired, purified before application.

7 Claims, 13 Drawing Sheets

```
  1 ATGGGCGTCTCTGCTGTTCTACTTCCTTTGTATCTCCTGTCTGGAGTCACCTCCGGACTG
-23 M  G  V  S  A  V  L  L  P  L  Y  L  L  S  G  V  T  S  G  L

61 GCAGTCCCCGCCTCGAGAAATCAATCCAGTTGCGATACGGTCGATCAGGGGTATCAATGC
    A  V  P  A  S  R  N  Q  S  S  C  D  T  V  D  Q  G  Y  Q  C
             -1 +1

121 TTCTCCGAGACTTCGCATCTTTGGGGTCAATACGCACCGTTCTTCTCTCTGGCAAACGAA
 18 F  S  E  T  S  H  L  W  G  Q  Y  A  P  F  F  S  L  A  N  E

181 TCGGTCATCTCCCCTGAGGTGCCCGCCGGATGCAGAGTCACTTTCGCTCAGGTCCTCTCC
 38 S  V  I  S  P  E  V  P  A  G  C  R  V  T  F  A  Q  V  L  S

241 CGTCATGGAGCGCGGTATCCGACCGACTCCAAGGGCAAGAAATACTCCGCTCTCATTGAG
 58 R  H  G  A  R  Y  P  T  D  S  K  G  K  K  Y  S  A  L  I  E

301 GAGATCCAGCAGAACGCGACCACCTTTGACGGAAAATATGCCTTCCTGAAGACATACAAC
 78 E  I  Q  Q  N  A  T  T  F  D  G  K  Y  A  F  L  K  T  Y  N

361 TACAGCTTGGGTGCAGATGACCTGACTCCCTTCGGAGAACAGGAGCTAGTCAACTCCGGC
 98 Y  S  L  G  A  D  D  L  T  P  F  G  E  Q  E  L  V  N  S  G

421 ATCAAGTTCTACCAGCGGTACGAATCGCTCACAAGGAACATCGTTCCATTCATCCGATCC
118 I  K  F  Y  Q  R  Y  E  S  L  T  R  N  I  V  P  F  I  R  S

481 TCTGGCTCCAGCCGCGTGATCGCCTCCGGCAAGAAATTCATCGAGGGCTTCCAGAGCACC
138 S  G  S  S  R  V  I  A  S  G  K  K  F  I  E  G  F  Q  S  T

541 AAGCTGAAGGATCCTCGTGCCCAGCCCGGCCAATCGTCGCCCAAGATCGACGTGGTCATT
158 K  L  K  D  P  R  A  Q  P  G  Q  S  S  P  K  I  D  V  V  I

601 TCCGAGGCCAGCTCATCCAACAACACTCTCGACCCAGGCACCTGCACTGTCTTCGAAGAC
178 S  E  A  S  S  S  N  N  T  L  D  P  G  T  C  T  V  F  E  D

661 AGCGAATTGGCCGATACCGTCGAAGCCAATTTCACCGCCACGTTCGTCCCCTCCATTCGT
198 S  E  L  A  D  T  V  E  A  N  F  T  A  T  F  V  P  S  I  R

721 CAACGTCTGGAGAACGACCTGTCCGGTGTGACTCTCACAGACACAGAAGTGACCTACCTC
218 Q  R  L  E  N  D  L  S  G  V  T  L  T  D  T  E  V  T  Y  L

781 ATGGACATGTGCTCCTTCGACACCATCTCCACCAGCACCGTCGACACCAAGCTGTCCCCC
238 M  D  M  C  S  F  D  T  I  S  T  S  T  V  D  T  K  L  S  P
```

FIG.2A

```
841  TTCTGTGACCTGTTCACCCATGACGAATGGATCAACTACGACTACCTCCAGTCCTTGAAA
258   F  C  D  L  F  T  H  D  E  W  I  N  Y  D  Y  L  Q  S  L  K

901  AAGTATTACGGCCATGGTGCAGGTAACCCGCTCGGCCCGACCCAGGGCGTCGGCTACGCT
278   K  Y  Y  G  H  G  A  G  N  P  L  G  P  T  Q  G  V  G  Y  A

961  AACGAGCTCATCGCCCGTCTGACCCACTCGCCTGTCCACGATGACACCAGTTCCAACCAC
298   N  E  L  I  A  R  L  T  H  S  P  V  H  D  D  T  S  S  N  H

1021 ACTTTGGACTCGAGCCCGGCTACCTTTCCGCTCAACTCTACTCTCTACGCGGACTTTTCG
318   T  L  D  S  S  P  A  T  F  P  L  N  S  T  L  Y  A  D  F  S

1081 CATGACAACGGCATCATCTCCATTCTCTTTGCTTTAGGTCTGTACAACGGCACTAAGCCG
338   H  D  N  G  I  I  S  I  L  F  A  L  G  L  Y  N  G  T  K  P

1141 CTATCTACCACGACCGTGGAGAATATCACCCAGACAGATGGATTCTCGTCTGCTTGGACG
358   L  S  T  T  T  V  E  N  I  T  Q  T  D  G  F  S  S  A  W  T

1201 GTTCCGTTTGCTTCGCGTTTGTACGTCGAGATGATGCAGTGTCAGGCGGAGCAGGAGCCG
378   V  P  F  A  S  R  L  Y  V  E  M  M  Q  C  Q  A  E  Q  E  P

1261 CTGGTCCGTGTCTTGGTTAATGATCGCGTTGTCCCGCTGCATGGGTGTCCGGTTGATGCT
398   L  V  R  V  L  V  N  D  R  V  V  P  L  H  G  C  P  V  D  A

1321 TTGGGGAGATGTACCCGGGATAGCTTTGTGAGGGGGTTGAGCTTTGCTAGATCTGGGGGT
418   L  G  R  C  T  R  D  S  F  V  R  G  L  S  F  A  R  S  G  G

1381 GATTGGGCGGAGTGTTTTGCTTAG
438   D  W  A  E  C  F  A  *
```

FIG. 2B

Polylinker sequences:

Eco RI　Kpn I　Sma I　Bam HI　Xba I　Xho I　Hind III
5'GGAATTCTGGTACCTCCCGGGAGGATCCATCTAGAGCTCGAGTAAGCTTC 3'
　　　　　　　　　　　　　　　　　　　Sac I oligonucleotide duplex A

```
                         NcoI            BamHI   HindIII
5' GGGTTTTTATTTTAATTTCTTCAAATACTTCCACCATGGGTAACGGATCCA    3'
3' CCCAAAAATAAAATTAAAGAAGTTTATGAAGGTGGTACCCATTGCCTAGGTTCGA 5'
``` oligonucleotide duplex B

```
                                                                                SphI  XhoI  BamHI
5' CATGAACTTCCTCAAGAGCTTCCCCTTTTATGCCTTCCTTGTTTTTGGCCAATACTTTGTAGCTGTTACGGCATGCTCGAG       3'
3'     TGAAGGAGTTCTCGAAGGGGAAAATACGGAAGGAACAAAAACCGGTTATGAAACATCGACAATGCCGTACGAGCTCCTAG    5'
``` oligonucleotide duplex C

```
   SphI             XhoI       PstI  BamHI
5'     CT CTGGCAGTCCCCGCCTCGAGCCCCCTGCAG     3'
3' GTACGA GACCGTCAGGGGCGGAGCTCGGGGGACGTCCTAG 5'
   PROB12 Mature phytase
   signal
   peptide
```

FIG. 4A

Oligonucleotide duplex D

```
          NcoI                            XhoI  EcoRV PstI
                                                      BglII        HindIII
      HisGlySerThrAla|LeuAlaValProAlaSer
   5' CATGGCTCTACAGCT CTGGCAGTCCCCGCCTCGAGGATATCCTGCAGATCTCCCCA 3'
   3'     CGAGATGTCGA GACCGTCAGGGGCGGAGCTCCTATAGGACGTCTAGAGGGGTTCGA 5'
      CruA signal     Mature phytase   Multiple cloning site
         peptide
```

Oligonucleotide duplex E

```
   5' AATTCAGATCTCCATGGATCGATGAGCT 3'
   3'     GTCTAGAGGTACCTAGCTAC     5'
```

FIG. 4B

EXPRESSION OF PHYTASE IN PLANTS

RELATED APPLICATIONS

This application is a Continuation-in-Part of U.S. application Ser. No. 08/693,709 filed Aug. 7, 1996 now U.S. Pat. No. 5,770,413, which is a continuation-in-part of U.S. Ser. No. 08/146,424 filed on Nov. 2, 1993, now U.S. Pat. No. 5,593,963 which is a continuation-in-part of U.S. application Ser. No. 07/756,864, filed Sep. 11, 1991, now abandoned, which is a Continuation-in-Part of U.S. application Ser. No. 07/586,765, filed Sep. 21, 1990, abandoned.

BACKGROUND OF THE DISCLOSURE

1. Technical Field

The present invention pertains to the production of phytase in transgenic plants and the use of the thus-produced phytase in industrial processes.

2. Background of the Invention

Phosphorus is an essential element for the growth of all organisms. In livestock production, feed must be supplemented with inorganic phosphorus in order to obtain a good growth performance of monogastric animals (e.g. pigs, poultry and fish).

In contrast, no inorganic phosphate needs to be added to the feedstuffs of ruminant animals. Microorganisms, present in the rumen, produce enzymes which catalyze the conversion of phytate (myo-inositolhexakis-phosphate) to inositol and inorganic phosphate.

Phytate occurs as a storage phosphorus source in virtually all feed substances originating from plants (for a review see: *Phytic acid, chemistry and applications,* E. Graf (ed.), Pilatus Press; Minneapolis, Minn., U.S.A. (1986)). Phytate comprises 1–3% of all nuts, cereals, legumes, oil seeds, spores and pollen. Complex salts of phytic acid are termed phytin. Phytic acid is considered to be an anti-nutritional factor since it chelates minerals such as calcium, zinc, magnesium, iron and may also react with proteins, thereby decreasing the bioavailability of proteins and nutritionally important minerals.

Phytate phosphorus passes through the gastrointestinal tract of monogastric animals and is excreted in the manure. Though some hydrolysis of phytate does occur in the colon, the thus-released inorganic phosphorus has no nutritional value since inorganic phosphorus is absorbed only in the small intestine. As a consequence, a significant amount of the nutritionally important phosphorus is not used by monogastric animals, despite its presence in the feed.

The excretion of phytate phosphorus in manure has further consequences. Intensive livestock production has increased enormously during the past decades. Consequently, the amount of manure produced has increased correspondingly and has caused environmental problems in various parts of the world. This is due, in part, to the accumulation of phosphate from manure in surface waters which has caused eutrophication.

The enzymes produced by microorganisms, which catalyze the conversion of phytate to inositol and inorganic phosphorus are broadly known as phytases. Phytase producing microorganisms comprise bacteria such as *Bacillus subtilis* (V. K. Paver and V. J. Jagannathan (1982) J. Bacteriol. 151, 1102) and Pseudomonas (D. J. Cosgrove (1970) Austral. J. Biol. Sci. 23, 1207); yeasts such as *Saccharomvces cerevisiae* (N. R. Nayini and P. Markakis (1984) Lebensmittel Wissenschaft und Technologie 17, 24); and fungi such as *Aspergillus terreus* (K. Yamada, Y. Minoda and S. Yamamoto (1986) Agric. Biol. Chem. 32, 1275). Various other Aspergillus species are known to produce phytase, of which, the phytase produced by *Aspergillus ficuum* has been determined to possess one of the highest levels of specific activity, as well as having better thermostability than phytases produced by other microorganisms (van Gorcom et al. (1991) European Patent Application 89202436.5, Publication No. 0 420 358, filed Sep. 27, 1989).

Phytases are also endogenously present in many plant species (see Loewus, F. A. (1990) In: *Plant Biology* vol. 9: "Inositol metabolism in plants" (eds. D. J. Morré, W. F. Boss, F. A. Loewus) 13). Gellatly, K. S. and Lefebvre, D. D. ((1990) Plant Physiology (supplement), 93, abstract 562) mention the isolation and characterization of a phytase cDNA clone obtained from potato tubers. Gibson, D. M. e al. and Christen, A. A. et al. ((1988) J. Cell Biochem., 12C abstracts L407 and L402, respectively) mention the synthesis of endogenous phytase during the germination of soybean seeds. However, plant phytases are normally produced in amounts insufficient for their application in industrial processes, per se.

The concept of adding microbial phytase to the feedstuffs of monogastric animals has been previously described (Ware, J. H., Bluff, L. and Shieh, T. R. (1967) U.S. Pat. No. 3,297,548; Nelson, T. S., Shieh, T. R., Wodzinski, R. J. and Ware, J. H. (1971) J. Nutrition 101, 1289). To date, however, application of this concept has not been commercially feasible, due to the high cost of the production of the microbial enzymes (Y. W. Han (1989) Animal Feed Sci. and Technol. 24, 345). For economic reasons, inorganic phosphorus is still added to monogastric animal feedstuffs.

Phytases have found other industrial uses as well. Exemplary of such utilities is an industrial process for the production of starch from cereals such as corn and wheat. Waste products comprising e.g. corn gluten feeds from such a wet milling process are sold as animal feed. During the steeping process phytase may be supplemented. Conditions (T≈50° C. and pH=5.5) are ideal for fungal phytases (see e.g. European Patent Application 0 321 004 to Alko Ltd.). Advantageously, animal feeds derived from the waste products of this process will contain phosphate instead of phytate.

It has also been conceived that phytases may be used in soy processing (see *Finase™ Enzymes By Alko,* a product information brochure published by Alko Ltd., Rajamäki, Finland). Soybean meal contains high levels of the anti-nutritional factor phytate which renders this protein source unsuitable for application in baby food and feed for fish, calves and other non-ruminants. Enzymatic upgrading of this valuable protein source improves the nutritional and commercial value of this material.

The possibility of using transgenic plants as a production system for valuable proteins has been proposed. Examples to date are the production of interferon in tobacco (Goodman, R. M., Knauf, V. C., Houck, C. M. and Comai, L. (1987) PCT/WO 87/00865), enkephalins in tobacco, *Brassica napus* and *Arabidopsis thaliana* (Vandekerckhove, J., Van Damme, J., Van Lijsebettens, M., Botterman, J., DeBlock, M., DeClerq, A., Leemans, J., Van Montagu, M. and Krebbers, E. (1989) Bio/Technol. 7, 929), antibodies in tobacco (Hiatt, A., Cafferkey, R. and Boedish, K. (1990) Nature 342, 76) and human serum albumin in tobacco and potato (Sijmons, P. C., Dekker, B. M. M., Schrammeijer, B., Verwoerd, T. C., van den Elzen, P. J. N. and Hoekema, A. (1990) Bio/Technol. 8, 217).

In practice, the transformation of an increasing number of plant species, especially dicotyledonous species (e.g.

tobacco, potato, tomato, Petunia, Brassica), has become a routine procedure for workers skilled in the art (Klee, H., Horsch, R. and Rogers, S. (1987) Annu. Rev. Plant Physiol. 38, 467; Gasser C. S. and Fraley, R. T. (1989) Science 244, 1293). Strategies for the expression of foreign genes in plants have become well established (Gasser and Fraley, supra). Regulatory sequences from plant genes have been identified that are used for the construction of chimeric genes that can be functionally expressed in plants and plant cells.

For the introduction of gene constructions into plants, several technologies are available, such as transformation with *Agrobacterium tumefaciens* or *Agrobacterium rhizogenes*. Using this strategy, a wide variety of plant tissues have been exploited, the choice being largely dependent on the plant species and its amenability in tissue culture. Successful examples are the transformation of protoplasts, microspores or pollen, and explants such as leaves, stems, roots, hypocotyls and cotyls. Furthermore, methods for direct DNA introduction in protoplasts and plant cells or tissues are used such as microinjection, electroporation, particle bombardment and direct DNA uptake (Gasser and Fraley, supra).

Proteins may be produced in plants using a variety of expression systems. For instance, the use of a constitutive promoter such as the 35S promoter of Cauliflower Mosaic Virus (CaMV) (Guilley, H., Dudley, R. K., Jonard, G., Balazs, E. and Richards, K. E. (1982) Cell 30, 763) will result in the accumulation of the expressed protein in all organs of the transgenic plant. Alternatively, use may be made of promoters from genes encoding proteins which are expressed in a highly tissue-specific and stage-specific manner (Higgins, T. J. V., (1984) Annu. Rev. Plant Physiol. 35, 191; Shotwell, M. A. and Larkins, B. A. (1989) In: *The biochemistry of plants* Vol. 15 (Academic Press, San Diego: Stumpf, P. K. and Conn, E. E., eds.), 297), i.e., the genes are expressed only in the target tissue and only during the desired stage of development.

It will be appreciated that an economical procedure for the production of phytase will be of significant benefit to, inter alia, the animal feed industry. One method of producing a more economical phytase would be to use recombinant DNA techniques to produce transgenic plants or plant organs capable of expressing phytase which could then in turn be added as such, for example, to animal food or feedstuffs for direct consumption by the animal. Alternatively, the phytase expressed in these transgenic plants or plant organs could be extracted and if desired, purified for the desired application.

SUMMARY OF THE INVENTION
Disclosure of the Invention

The present invention provides for the expression of phytase in transgenic plants or plant organs and methods for the production of such plants. This is achieved via the introduction into the plant of an expression construct comprising a DNA sequence encoding a protein having phytase activity.

The DNA expression constructs provided by the present invention for the transformation of plants are under the control of regulatory sequences which are capable of directing the expression of phytase. These regulatory sequences may also include sequences capable of directing transcription in plants, either constitutively, or stage and/or tissue specific, depending on the use of the plant or parts thereof.

The transgenic plants and plant organs provided by the present invention may be applied to a variety of industrial processes either directly, e.g. in animal food or feedstuffs or alternatively, the expressed phytase may be extracted and if desired, purified before application.

DESCRIPTION OF PREFERRED EMBODIMENTS

BRIEF DESCRIPTION OF THE DRAWINGS

FIG. 2 shows the nucleotide sequence of the translated region of the phytase cDNA fragment and the derived amino acid sequence of the phytase protein; the start of the mature phytase protein is indicated as position +1.

FIG. 4 shows the sequences of oligonucleotide duplexes used in cloning.

DETAILED DESCRIPTION OF THE INVENTION

Figure 1:
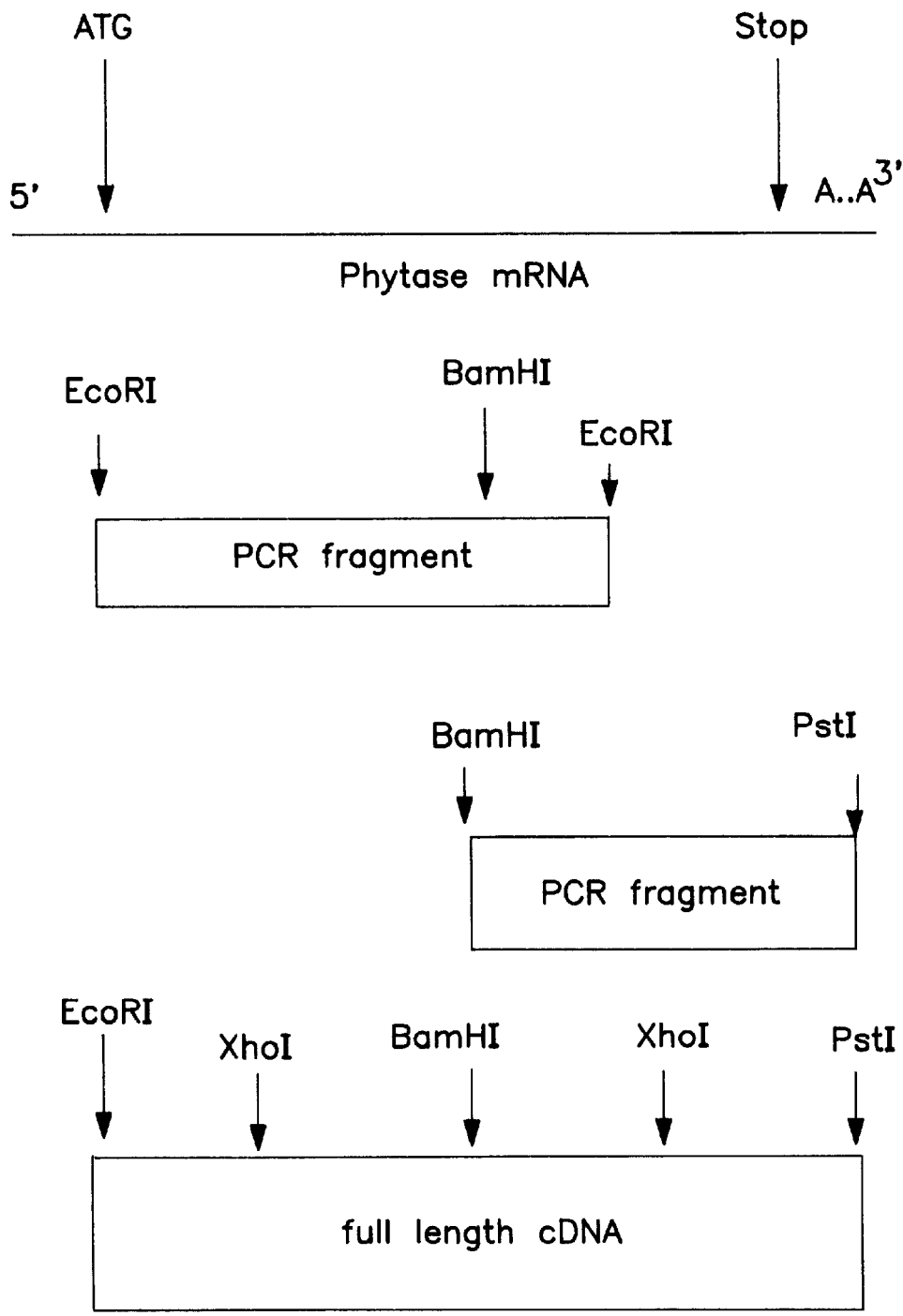
FIG. 1 is a schematic showing the strategy for cloning phytase cDNA.
Figure 3:
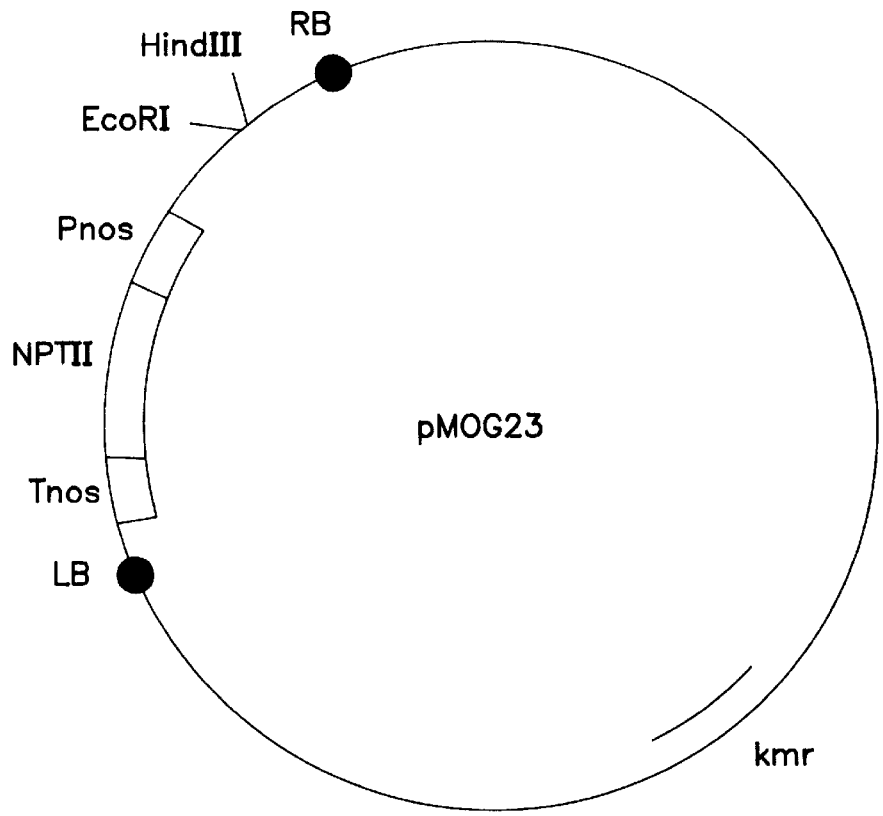
FIG. 3 is a diagram of binary vector pMOG23.

According to the present invention, transgenic plants or plant organs are obtained in which phytase is produced. This is achieved via the introduction into the plant of an expression construct comprising a DNA sequence encoding a protein having phytase activity.

DNA expression constructs are provided by the present invention for the stable transformation of plants with a gene encoding a phytase. These constructs comprise a DNA sequence encoding a phytase which is operably linked to regulatory sequences which are capable of directing the expression of phytase. These regulatory sequences may also include sequences capable of directing transcription in plants, either constitutively, or stage and/or tissue specific, depending on the use of the plant or parts thereof.

The expression constructs provided by the present invention may be inserted into a vector, preferably a plasmid, used in bacteria-mediated transformation of the selected plant host. The expression construct is then preferably integrated into the genome of the plant host.

Within the context of the present invention, the term phytase embraces a family of enzymes which catalyze reactions involving the liberation of inorganic phosphorus from various myoinositol phosphates. This is understood to embrace all proteins having phytase activity.

The DNA sequence encoding phytase may be obtained from a variety of sources such as microbial, plant or animal sources. Preferably, the DNA sequence is obtained from a microbial source such as the filamentous fungus Aspergillus. Most preferred DNA sequences are obtained from *Aspergillus ficuum, Aspergillus niger, Aspergillus awamori* and *Aspergillus nidulans*.

The cloning of a gene or a cDNA encoding a phytase protein may be achieved using various methods. One method is by purification of the phytase protein, subsequent determination of the N-terminal and several internal amino acid sequences and screening of a genomic or cDNA library of the organism producing the phytase, using oligonucleotide probes based on the amino acid sequences.

If at least a partial sequence of the gene is known, this information may be used to clone the corresponding cDNA using, for instance, the polymerase chain reaction (PCR) (*PCR Technology: Principles and Applications for DNA Amplification*, (1989) H. A. Ehrlich, ed., Stockton Press, New York).

It will be evident to those skilled in the art that the cloned phytase gene described above may be used in heterologous hybridization experiments, directed to the isolation of phytase encoding genes from other micro-organisms.

In another aspect, the cloned phytase gene described above may be used as starting materials for the construction of "second generation" phytases. "Second generation" phytases are phytases, altered by mutagenesis techniques (e.g. site-directed mutagenesis), which have properties that differ from those of wild-type phytases or recombinant phytases such as those produced by the present invention. For example, the temperature or pH optimum, specific activity or substrate affinity may be altered so as to be better suited for application in a defined process.

The isolation of the cDNA encoding phytase enables the construction of expression constructs capable of directing the production of phytase in the selected plant host via the application of recombinant DNA techniques such as the exchange of regulatory elements such as e.g. promoters, secretional signals, or combinations thereof.

Phytase may be produced constitutively in the transgenic plants during all stages of development. Depending on the use of the plant or plant organs, the enzymes may be expressed in a stage-specific manner, for instance during tuber formation or fruit development. Also, depending on the use, the enzymes may be expressed tissue-specifically, for instance in plant organs such as fruit, tubers, leaves or seeds.

Transgenic plants, as defined in the context of the present invention include plants (as well as parts and cells of said plants) and their progeny, which have been genetically modified using recombinant DNA techniques to cause or enhance production of a phytase in the desired plant or plant organ.

In the context of the present invention, the phrase "an enhanced amount of phytase" refers specifically to a statistically significant amount of plant tissue which, on average, contain a statistically significant greater amount of phytase as compared with the average amount of phytase enzyme found in an equal amount of non-modified plant tissue.

Within the context of the present invention, plants to be selected include, but are not limited to crops producing edible flowers such as cauliflower (*Brassica oleracea*, artichoke (*Cynara scolymus*), fruits such as apple (Malus, e.g. *domesticus*), banana (Musa, e.g. *acuminata*), berries (such as the currant, Ribes, e.g. *rubrum*), cherries (such as the sweet cherry, Prunus, e.g. *avium*), cucumber (Cucumis, e.g. *sativus*), grape (Vitis, e.g. *vinifera*), lemon (*Citrus limon*), melon (*Cucumis melo*), nuts (such as the walnut, Jualans, e.g. *reaia*; peanut, *Arachis hypogeae*), orange (Citrus, e.g. *maxima*), peach (Prunus, e.g. *persica*), pear (Pyra, e.g. *communis*), plum (Prunus, e.g. *domestica*), strawberry (Fraaaria, e.g. *moschata*), tomato (LycoDersicon, e.g. *esculentum*), leafs, such as alfalfa (Medicago, e.g. *sativa*), cabbages (e.g. *Brassica oleracea,*) endive (Cichoreum, e.g. *endivia*), leek (Allium, e.g. *porrum*), lettuce (Lactuca, e.g. *sativa*), spinach (Spinacia e.g. *oleraceae*), tobacco (Nicotiana, e.g. *tabacum*), roots, such as arrowroot (Maranta e.g. *arundinacea*), beet (Beta, e.g. *vularis*), carrot (Daucus, e.g. *carota*), cassava (Manihot, e.g. *esculenta*), turnip (Brassica, e.g. *rapa*), radish (Raphanus, e.g. *aivus*), yam (Dioscorea, e.g. *esculenta*), sweet potato (*Ipomoea batatas*) and seeds, such as bean (Phaseolus, e.g. *vulaaris*), pea (Pisum, e.g. *sativum*), soybean (Glycin, e.g. *max*), wheat (Triticum, e.g. *aestivum*), barley (Hordeum, e.g. *vulgare*), corn (Zea, e.g. *mays*), rice (Orvza, e.g. *sativa*), rapeseed (*Brassica nanus*), millet (Panicum L.), sunflower (*Helianthus annus*), oats (*Avena sativa*), tubers, such as kohlrabi (Brassica, e.g. *oleraceae*), potato (Solanum, e.g. *tuberosum*) and the like.

The choice of the plant species is primarily determined by the intended use of the plant or parts thereof and the amenability of the plant species to transformation. Several techniques are available for the introduction of the expression construct containing the phytase-encoding DNA sequence into the target plants. Such techniques include but are not limited to transformation of protoplasts using the calcium/polyethylene glycol method, electroporation and microinjection or (coated) particle bombardment (Potrykus, I. (1990) Bio/Technol. 8, 535).

In addition to these so-called direct DNA transformation methods, transformation systems involving vectors are widely available, such as viral vectors (e.g. from the Cauliflower Mosaic Virus (CaMV) and bacterial vectors (e.g. from the genus Agrobacterium) (Potrykus, supra). After selection and/or screening, the protoplasts, cells or plant parts that have been transformed can be regenerated into whole plants, using methods known in the art (Horsch, R. B., Fry, J. E., Hoffmann, N. L., Eichholtz, D., Rogers, S. G. & Fraley, R. T. (1985) Science 2, 1229). The choice of the transformation and/or regeneration techniques is not critical for this invention.

For dicots, a preferred embodiment of the present invention uses the principle of the binary vector system (Hoekema, A., Hirsch, P. R., Hooykaas, P. J. J. and Schilperoort, R. A. (1983) Nature 3, 179; Schilperoort, R. A., Hoekema, A. and Hooykaas, P. J. J. (1984) European Patent Application No. 0 120 516) in which Agrobacterium strains are used which contain a vir plasmid with the virulence genes and a compatible plasmid containing the gene construct to be transferred. This vector can replicate in both *E. coli* and in Agrobacterium, and is derived from the binary vector Bin19 (Bevan, M. (1984) Nucl. Acids Res. 12, 8711) which is altered in details that are not relevant for this invention. The binary vectors as used in this example contain between the left- and right-border sequences of the T-DNA, an identical NPTII-gene coding for kanamycin resistance (Bevan, supra) and a multiple cloning site to clone in the required gene constructs.

The transformation and regeneration of monocotyledonous crops is not a standard procedure. However, recent scientific progress shows that in principle monocots are amenable to transformation and that fertile transgenic plants can be regenerated from transformed cells. The development of reproducible tissue culture systems for these crops, together with the powerful methods for introduction of genetic material into plant cells has facilitated transformation. Presently the methods of choice for transformation of monocots are microprojectile bombardment of explants or suspension cells, and direct DNA uptake or electroporation of protoplasts. For example, transgenic rice plants have been successfully obtained using the bacterial hph gene, encoding hygromycin resistance, as a selection marker. The gene was introduced by electroporation (Shimamoto, K., Terada, R., Izawa, T. and Fujimoto, H. (1989) Nature 338, 274). Transgenic maize plants have been obtained by introducing the *Streptomyces hygroscopicus* bar gene, which encodes phosphinothricin acetyltransferase (an enzyme which inactivates the herbicide phosphinothricin), into embryogenic cells of a maize suspension culture by microparticle bombardment (Gordon-Kamm, W. J., Spencer, T. M., Mangano, M. L., Adams, T. R., Daines, R. J., Start, W. G., O'Brien, J. V., Chambers, S. A., Adams Jr., W. R., Willets, N. G., Rice, T. B., Mackey, C. J., Krueger, R. W., Kausch, A. P. and Lemaux, P. G. (1990) The Plant Cell 2, 603). The introduction of genetic material into aleurone protoplasts of other monocot crops such as wheat and barley has been reported (Lee, B., Murdoch, K., Topping, J., Kreis, M. and Jones, M. G. K. (1989) Plant Mol. Biol. 13, 21). Wheat plants have been regenerated from embryogenic suspension culture by selecting only the aged compact and nodular embryogenic callus tissues for the establishment of the embryogenic suspension cultures (Vasil, V., Redway, F. and Vasil, I. K. (1990) Bio/Technol. 8, 429). The combination with transformation systems for these crops enables the application of the present invention to monocots. These methods may also be applied for the transformation and regeneration of dicots.

Expression of the phytase construct involves such details as transcription of the gene by plant polymerases, translation of mRNA, etc. that are known to persons skilled in the art of recombinant DNA techniques. Only details relevant for the proper understanding of this invention are discussed below.

Regulatory sequences which are known or are found to cause expression of phytase may be used in the present invention. The choice of the regulatory sequences used depends on the target crop and/or target organ of interest. Such regulatory sequences may be obtained from plants or plant viruses, or may be chemically synthesized. Such regulatory sequences are promoters active in directing transcription in plants, either constitutively or stage and/or tissue specific, depending on the use of the plant or parts thereof. These promoters include, but are not limited to promoters showing constitutive expression, such as the 35S promoter of Cauliflower Mosaic Virus (CaMV) (Guilley et al. (1982) Cell 30, 763), those for leaf-specific expression, such as the promoter of the ribulose bisphosphate carboxylase small subunit gene (Coruzzi et al., (1984) EMBO J. 3, 1671), those for root-specific expression, such as the promoter from the glutamine synthase gene (Tingey et al. (1987) EMBO J., 6, 3565), those for seed-specific expression, such as the cruciferin A promoter from *Brassica nanus* (Ryan et al. (1989) Nucl. Acids Res. 17, 3584), those for tuber-specific expression, such as the class-I patatin promoter from potato (Rocha-Sosa et al, (1989) EMBO J. 8, 23; Wenzler et al, (1989) Plant Mol. Biol. 12, 41) or those for fruit-specific expression, such as the polygalacturonase (PG) promoter from tomato (Bird et al, (1988) Plant Mol. Biol. 11, 651).

Other regulatory sequences such as terminator sequences and polyadenylation signals include any such sequence functioning as such in plants, the choice of which is within the level of the skilled artisan. An example of such sequences is the 3' flanking region of the nopaline synthase (nos) gene of *Agrobacterium tumefaciens* (Bevan, M., supra).

The regulatory sequences may also include enhancer sequences, such as found in the 35S promoter of CaMV, and mRNA stabilizing sequences such as the leader sequence of Alfalfa Mosaic Virus (AlMV) RNA4 (Brederode, F. T., Koper-Zwarthoff, E. C. & Bol, J. F. (1980) Nucl. Acids Res. 8, 2213) or any other sequences functioning in a like manner.

The phytase should be expressed in an environment that allows for stability of the expressed protein. The choice of cellular compartments, such as cytosol, endoplasmic reticulum, vacuole, protein body or periplasmic space can be used in the present invention to create such a stable environment, depending on the biophysical parameters of the phytase. Such parameters include, but are not limited to pH-optimum, sensitivity to proteases or sensitivity to the molarity of the preferred compartment.

To obtain expression in the cytoplasm of the cell, the expressed enzyme should not contain a secretory signal peptide or any other target sequence. For expression in chloroplasts and mitochondria the expressed enzyme should contain a specific so-called transit peptide for import into these organelles. Targeting sequences that can be attached to the enzyme of interest in order to achieve this are known (Smeekens et al, (1990) T. I. B. S. 15, p.73; van den Broeck et al., (1985) Nature 313, 358; Schreier et al., (1985) EMBO J. 4, 25). If the activity of the enzyme is desired in the vacuoles a secretory signal peptide has to be present, as well as a specific targeting sequence that directs the enzyme to these vacuoles (Tague et al, (1988) Plant Phys. 86, 506). The same is true for the protein bodies in seeds. The DNA sequence encoding the enzyme of interest should be modified in such a way that the enzyme can exert its action at the desired location in the cell.

To achieve extracellular expression of the phytase, the expression construct of the present invention utilizes a secretory signal sequence. Although signal sequences which are homologous (native) to the plant host species are preferred, heterologous signal sequences, i.e. those originating from other plant species or of microbial origin, may be used as well. Such signal sequences are known to those skilled in the art. Appropriate signal sequences which may be used within the context of the present invention are disclosed in Walter, P. and Blobel, G. (1986) Biochem. Soc. Symp., 47, 183; Von Heijne, G. (1986) J. Mol. Biol., 189, 239; and Sijmons, P.C., Dekker, B. M. M., Schrammeijer, B., Verwoerd, T. C., van den Elzen, P. J. M. and Hoekema, A. (1990) Bio/Technol., 8, 217.

All parts of the relevant DNA constructs (promoters, regulatory-, secretory-, stabilizing-, targeting- or termination sequences) of the present invention may be modified, if desired, to affect their control characteristics using methods known to those skilled in the art.

It is pointed out that plants containing phytase obtained via the present invention may be used to obtain plants or plant organs with yet higher phytase levels. For example, it may be possible to obtain such plants or plant organs by the use of somoclonal variation techniques or by cross breeding techniques. Such techniques are well known to those skilled in the art.

In one embodiment of the present invention, a double-stranded cDNA encoding phytase is prepared from mRNA isolated from *Aspergillus ficuum*. The DNA construct is placed under the control of regulatory sequences from the gene encoding the 12S storage protein cruciferin from *Brassica napus*. The construct is thereafter subcloned into a binary vector such as pMOG23 (in *E. coli* K-12 strain DH5α, deposited at the Centraal Bureau voor Schimmelcultures, Baarn, The Netherlands on Jan. 29, 1990 under accession number CBS 102.90). This vector is introduced into *Agrobacterium tumefaciens* which contains a disarmed Ti plasmid. Bacterial cells containing this construct are co-cultivated with tissues from tobacco or Brassica plants, and transformed plant cells are selected by nutrient media containing antibiotics and induced to regenerate into differentiated plants on such media. The resulting plants will produce seeds that contain and express the DNA construct.

In another embodiment of the present invention, the phytase-encoding DNA construct is placed under the control of regulatory sequences from the 35S promoter of Cauliflower Mosaic Virus (CaMV). The construct is thereafter subcloned into a binary vector. This vector is then introduced into *Agrobacterium tumefaciens* which contains a disarmed Ti plasmid. Bacterial cells containing this construct are co-cultivated with tissues from tobacco or Brassica plants, and transformed plant cells are selected by nutrient media containing antibiotics and induced to regenerate into differentiated plants on such media. The resulting plants contain and express the DNA construct constitutively.

Phytase activity may be measured via a number of assays, the choice of which is not critical to the present invention. For example, the phytase enzyme activity of the transgenic plant tissue may be tested with an ELISA-assay, Western blotting or direct enzyme assays using calorimetric techniques or native gel assays.

The plant or plant organ containing phytase, as produced via the present invention may be used in a variety of industrial processes requiring the action of a phytase.

The plants or plant organs containing phytase produced according to the present invention may be used in industrial processes requiring the action of a phytase. Examples of such applications are in feed additives fur non-ruminants, in soy processing, or in the production of inositol or inositol-phosphates from phytate. Other industrial processes using substrates that contain phytate such as the starch industry and in fermentation industries, such as the brewing industry. Chelation of metal ions by phytate may cause these minerals to be unavailable for the production microorganisms. Enzymatic hydrolysis of phytate prevents these problems.

Phytase produced in plants can also be used in a process for steeping corn or sorghum kernels. The plant tissue may be ground before adding to steeping corn. Phytase liberated from the plant tissue can act on phytin, which is present in many corn preparations. Degradation of phytin in steeping corn is beneficial for the added commercial value of corn steep liquor, which is used as animal feed or as a nutrient in microbial fermentations. Furthermore, the degradation of phytin can prevent problems relating to the accumulation of deposits in filters, pipes, reactor vessels, etc. during concentration, transport and storage of corn steep liquor (Vaara, T. at Al. (1989) European Patent Application 0 321 004). The action of phytase can also accelerate the steeping process and the separation processes involved in corn wet milling.

The plants or plant organs may be used directly, i.e. without further processing, or may first be processed via conventional means such as grinding to the desired consistency before application.

Alternatively, the phytase may be extracted from the plant or plant organ and, if desired, purified before use using conventional extraction methods and purification techniques.

The production of phytases in plants which are compatible with the intended application provides convenience and will reduce production costs as compared to that of microbial phytases in order to allow its economical application, e.g. in animal feed, which eventually will lead to a price/in vivo performance ratio competitive with inorganic phosphate. As a further benefit, the phosphorus content of manure will be considerably decreased.

It will be appreciated that the application of phytases, available at a price competitive with inorganic phosphate, will increase the degrees of freedom for the compound feed industry to produce a high quality feed. For example, when feed is supplemented with phytase, the addition of inorganic phosphate may be omitted and the contents of various materials containing phytate may be increased.

The following examples are provided so as a to give those of ordinary skill in the art a complete disclosure and description of how to make and use the invention and are not intended to limit the scope of what the inventors regard as their invention. Efforts have been made to ensure accuracy with respect to numbers used (e.g., amounts, temperature, pH, etc.) but some experimental errors and deviation should be accounted for. Unless indicated otherwise, temperature is in degrees Centrigrade and pressure is at or near atmospheric.

Example 1

Isolation of Poly $A^+$ RNA from *Aspergillus ficuum*

*A. ficuum* strain NRRL 3135 is grown in a medium containing 22.72 g/l maize flour (amylase treated at pH 7 at 85° C. during 15 minutes), 9.36 g/l glucose, 2.9 g/l $KNO_3$, 0.142 g/l KCl, 0.142 g/l $MgSO_4.7H_2O$ and 56.8 mg/l $FeSO_4.7H_2O$. After 6 days the mycelium is harvested.

Dry mycelium (0.5 g) is frozen with liquid nitrogen and ground. Subsequently the material is homogenized with an Ultra turrax (full speed, 1 minute) at 0° C. in 3 M LiCl, 6 M Urea and maintained overnight at 4° C. as described by Auffray and Rougeon (1980) Eur. J. Biochem. 107, 303. Total cellular RNA is obtained after centrifugation at 16,000×g, which is followed by two successive extractions with phenol:chloroform:isoamylalcohol (50:48:2). The RNA is precipitated with ethanol and redissolved in 1 ml 10 mM Tris-HCl (pH 7.4), 0.5% SDS. For poly $A^+$ selection the total RNA sample is heated for 5 minutes at 65° C., adjusted to 0.5 M NaCl and subsequently applied to an oligo(dT)-cellulose column. After several washes with an solution containing 10 mM Tris pH 7.0, 1 mM EDTA and 0.1 mM NaCl, the poly $A^+$ RNA is collected by elution with 10 mM Tris pH 7.0 and 1 mM EDTA.

Example 2

Preparation and Cloning of a cDNA Encoding Phytase

For the synthesis of the first strand of the cDNA 5 pg of poly $A^+$ RNA, isolated according to Example 1, is dissolved in 16.5 μl $H_2O$ and the following components are added: 2.5 μl RNasin (30 U/μl), 10 μl of a buffer containing 50 mM Tris-HCl pH 7.6, 6 mM $MgCl_2$ and 40 mM KCl, 2 μl 1 M KCl, 5 μl 0.1 M DTT, 0.5 μl 1 oligo(dT)$_{12-18}$ (2.5 mg/ml), 5 μl 8 mM dNTP-mix, 5 μl BSA (1 mg/ml) and 2.5 μl Moloney MLV reverse transcriptase (200 U/μl). The mixture is incubated for 30 minutes at 37° C. and the reaction is stopped by addition of 10 μl 0.2 M EDTA and 50 μl $H_2O$. An extraction is performed using 110 μl chloroform and after centrifugation for 5 minutes 5 M $NH_4Ac$ and 440 μl absolute ethanol (−20° C.) are added to the supernatant. Precipitation is done in a dry ice/ethanol solution for 30 minutes. After centrifugation (10 minutes at 0° C.) the cDNA/mRNA pellet is washed with 70% ice-cold ethanol. The pellet is dried and dissolved in 20 µl of H₂O.

Isolation of the cDNA encoding phytase is performed with the Polymerase Chain Reaction (PCR) in two fragments. The two fragments are combined, using the BamHI site within the gene to create a full length cDNA. The strategy for the cloning of the phytase cDNA is shown in FIG. 1.

Partial sequencing of the phytase gene (Van Gorcom et al., supra), reveals the presence of d BamHI site at approximately 800 basepairs from the initiation codon. The nucleotide sequence around this BamHI site, as well as the nucleotide sequence preceding the start codon and the nucleotide sequence after the stop codon of the phytase gene are used to design oligonucleotides for the PCR.

The polymerase chain reaction is performed according to the supplier of Taq-polymerase (Cetus) using 1.5 µl of the solution containing the reaction product of the first strand synthesis and 0.5 µg of each of the oligonucleotides. Amplification is performed in a DNA amplifier of Perkin Elmer/Cetus. After 25 cycles of 2 minutes at 94° C., 2 minutes at 55° C., and 3 minutes at 72° C. the reaction mixture is deproteinized by subsequent phenol and chloroform extractions. The DNA is precipitated, redissolved in a buffer containing 10 mM Tris, pH 7 and 0.1 mM EDTA and subsequently digested with suitable restriction enzymea For the amplification of the fragment encoding the N-terminal part of the protein, the two following oligonucleotides are used:
Oligo 1: 5' GGGTAGAATTCAAAAATGGGCGTCTCTGCTGTTCTA 3'
Oligo 2: 5' AGTGACGAATTCGTGCTGGTGGAGATGGTGTCG 3'

The amplified fragment is digested with EcoRI and cloned into the EcoRI site of pTZ18R (purchased from Pharmacia). Restriction site mapping and nucleotide sequencing demonstrate the authenticity of the fragment. The resulting plasmid is named pGB925.

For the amplification of the second fragment, the following two oligonucleotides are used:
Oligo 3: 5' GAGCACCAAGCTGAAGGATCC 3'
Oligo 4: 5' AAACTGCAGGCGTTGAGTGTGATTGTTTAAAGGG 3'

The amplified fragment is digested with BamHI and PstI and subsequently cloned into pTZ18R, which has been digested with BamHI and PstI. Restriction site mapping and nucleotide sequencing show that the correct fragment is isolated. The resulting plasmid is named pGB926.

In order to isolate a full length cDNA, pGB925 is digested with EcoRI and BamHI and the fragment containing the phytase encoding DNA is isolated. This fragment is cloned into plasmid pGB926, which has been digested with EcoRI and BamHI, resulting in plasmid pGB927. Plasmid pGB927 contains a full length cDNA encoding phytase, with an approximate size of 1.8 kbp. The sequence of the cDNA region encoding the phytase protein and the derived amino acid sequence of the phytase protein are depicted in FIG. 2.

Example 3

Construction of the Binary Vector pMOG23.

In this example the construction of the binary vector pMOG23 (in *E. coli* K-12 strain DH5α, deposited at the Centraal Bureau voor Schimmel-cultures on Jan. 29, 1990 under accession number CBS 102.90) is described.

The binary vector pMOG23 (FIG. 2) is a derivative of vector Bin19 (Bevan, M., supra). To obtain pMOG23, the vector Bin19 is changed in a way not essential for the present invention, using techniques familiar to those skilled in the art of molecular biology.

First, the positions of the left border (LB) and the right border (RB) are switched with reference to the neomycine phosphotransferase gene II (NPTII gene). Secondly, the orientation of the NPTII gene is reversed giving transcription in the direction of LB. Finally, the polylinker of Bin19 is replaced by a polylinker with the following restriction enzyme recognition sites: EcoRI, KpnI, SmaI, BamHI, XbaI, SacI, XhoI, and HindIII.

Example 4

Cloning of the Phytase cDNA of *Aspergillus ficuum* in an Expression Construct for Constitutive Expression in Plants The phytase gene from *Aspergillus ficuum* is tailored and cloned in an expression construct for constitutive expression downstream of the Cauliflower Mosaic Viris 35S promoter. The expression construct also contains the coding information for a signal peptide sequence of plant origin.

The phytase cDNA is cloned into the expression construct as present on plasmid pMOG29 (described under a)). Subsequently the entire construct is introduced into the binary vector pMOG23 and transferred to *Agrobacterium tumefaciens* strain LBA4404.

a) Construction of expression vector pMOG29

The expression construct of ROK1 (Baulcombe et al., (1986) Nature 321, 446) is cloned as an EcoRI/HindIII fragment into pUC18. This construct contains the Cauliflower Mosaic Virus (CaMV) 35S promoter on an EcoRI/BamHI fragment and the nopaline synthase (nos) transcription terminator on a BamHI/HindIII fragment. The promoter fragment consists of the sequence from −800 to +1 of the CaMV 35S promoter. Position +1, which is included, is the transcription initiation site (Guilley at al., supra). The sequence upstream of the NcoI site at position −512 is deleted and this site is changed into an EcoRI site. This is done by cutting the expression construct present in pUC18 with NcoI, filling in the single-stranded ends with Klenow polymerase and ligation of an EcoRI linker. The resulting plasmid is cut with EcoRI, resulting in the deletion of the EcoRI fragment carrying the sequences of the 35S promoter upstream of the original NcoI site. The BamHI/HindIII fragment, containing the nos terminator is replaced by a synthetic DNA fragment (oligonucleotide duplex A, FIG. 4) containing the leader sequence of RNA4 of Alfalfa Mosaic Virus (AlMV) (Brederode et al., supra). This is done by cleavage with BamHI, followed by cleavage with HindIII and ligation of the synthetic DNA fragment. The BamHI site and three upstream nucleotides are deleted by site-directed mutagenesis. In the resulting plasmid, the BamHI/HindIII fragment containing the nos terminator sequence is reintroduced. The gene encoding β-glucuronidase (originating from plasmid pRAJ 275; Jefferson, R. A. (1987) Plant Mol. Biol. Reporter 5, 387) was ligated in as an NcoI/BamHI fragment, resulting in plasmid pMOG14. From the literature it is known that duplication of the sequence between −343 and −90 increases the activity of the 35S promoter (Kay, R., Chan, A., Dayly, M. & McPherson, J. (1987) Science 236, 1299). To obtain a promoter fragment with a double, so-called enhancer sequence, the following steps, known to those skilled in the art, are carried out. From plasmid pMOG14, the enhancer fragment is isolated on an AccI/

Figure 5:
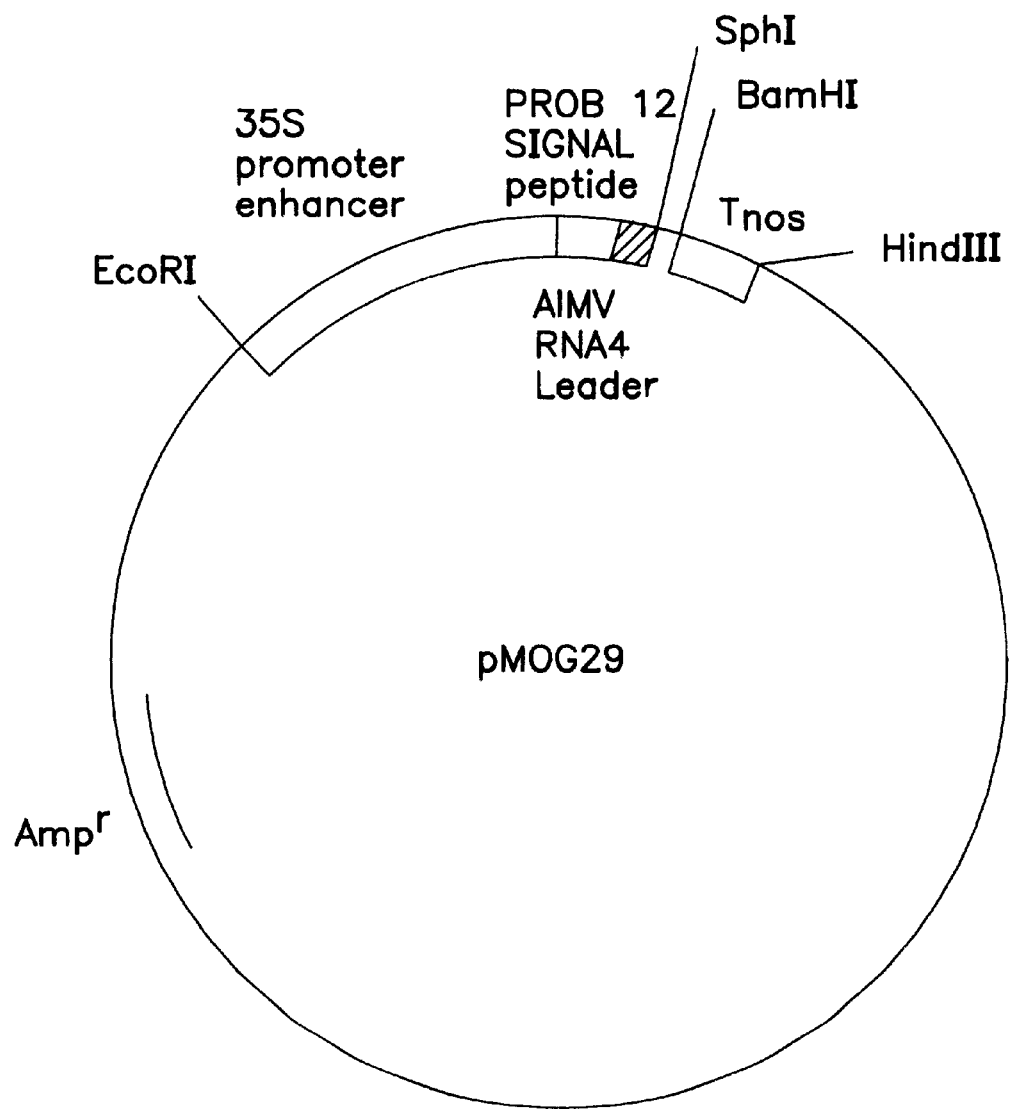
FIG. 5 is a diagram of plasmid pMOG29. Plasmid pUC18 containing an expression cassette for constitutive expression in plants and a sequence encoding a tobacco signal peptide.

EcoRI fragment and subsequently blunt-ended with Klenow polymerase. The obtained fragment is introduced in pMOG14 cut with EcoRI and blunt-ended, in such a way that the border between the blunt-ended EcoRI and AccI sites generate a new EcoRI site. The resulting plasmid (pMOG18) contains the 35S promoter with a double enhancer sequence, the leader sequence of RNA4 from AlMV and the nos terminator in an expression construct still present on an EcoRI/HindIII fragment. Finally, the NcoI/BamHI fragment encoding β-glucuronidase is replaced with the synthetic DNA fragment B (FIG. 4), derived from the PROB12 cDNA (Cornelissen, B. J. C., Hooft van Huijsduijnen, R. A. M. & Bol, J. F. (1986) Nature 321, 531). This fragment B encodes the PR-protein PR-S signal peptide sequence from tobacco Samsun NN. An SphI site is created in the signal peptide encoding DNA sequence by changing one nucleotide. This change does not alter the amino acid sequence of the encoded PR-S signal peptide. The resulting plasmid is called pMOG29 (FIG. 5).

b) Cloning of the phytase gene from *Aspergillus ficuum* in the binary vector

Oligonucleotide duplex C (FIG. 4) is cloned into plasmid pMOG29, digested with SphI and BamHI, resulting in plasmid pMOG407. The oligonucleotide duplex contains the coding information for the final 2 amino acids of the signal peptide of PR-S, followed by the first 6 amino acids of mature phytase.

The plasmid pGB927, which contains the full length phytase cDNA, is digested with XhoI (partially) and PstI. The XhoI/PstI fragment comprising the DNA sequences encoding mature phytase from amino acid 6 onward is cloned into plasmid pMOG407 linearized with XhoI and PstI, resulting in plasmid pMOG417. The entire construct, containing the chimaeric phytase gene, is inserted as an EcoRI/HindIII fragment into the binary vector pMOG23 linearized with EcoRI and HindIII. The resulting binary plasmid pMOG413 is mobilized, in a triparental mating with the *E. coli* K-12 strain RK2013 (containing plasmid pRK2013) (Ditta, G., Stanfield, S., Corbin, D. & Helinski, D. R. (1980) Proc. Natl. Acad. Sci. USA 77, 7347), into *Agrobacterium tumefaciens* strain LBA4404 that contains a plasmid with the virulence genes necessary for T-DNA transfer to the plant.

Example 5

Transient Expression of Chimaeric Phytase Gene in Tobacco Protoplasts

Protoplasts of tobacco are transformed with plasmid DNA carrying the chimaeric phytase gene under regulation of the constitutive CaMV 35S promoter. After 72 hours treated protoplasts are assayed for transient expression of the introduced phytase gene using the phytase activity assay.

Protoplasts are prepared from axenically grown 1–2 months old tobacco plants (*Nicotiana tabacum* SR1). The entire procedure is described by Rodenburg, K. W., DeGroot, M. J. A., Schilperoort, R. A. & Hooykaas, P. J. J. ((1989) Plant Mol. Biol. 13, 711). For transformation a number of $5 \times 10^5$ protoplasts is electroporated with 40 μg DNA of plasmid pMOG417). After electroporation protoplasts are resuspended in 3 ml of K3G medium. For the phytase activity assay protoplasts are pelleted and the 3 ml of supernatant is dialyzed overnight against an excess of water. The dialysate is freeze-dried and resuspended in 300 μl 25 mM sodium-acetate pH 5.5. The assay is then carried out as described in detail in Example 10, with the only exception that instead of the 250 mM Glycine HCl buffer pH 2.5, a 25 mM sodium acetate buffer pH 5.5 is used.

In these experiments, one phytase unit (PTU) is defined as 1 μmol of phosphate released from 1.5 mM sodium phytate solution per minute at 37° C. at pH 5.5.

In untreated protoplasts no detectable activity is found. Protoplasts electroporated with plasmid pMOG417 show an activity of 0.26 PTU per mg protein in the supernatant.

Example 6

Stable Expression of a Chimaeric Phytase Gene in Tobacco Plants Under the Control of the CaMV 35S Promoter Tobacco is transformed by cocultivation of plant tissue with *Agrobacterium tumefaciens* strain LBA4404 containing the binary vector pMOG413 with the chimaeric phytase gene under regulation of the CaMV 35S promoter. Transformation is carried out using cocultivation of tobacco (*Nicotiana tabacum* SR1) leaf discs according to Horsch et al., supra. Transgenic plants are regenerated from shoots that grow on selection medium (100 mg/l) kanamycin), rooted and transferred to soil. Young plants are assayed for NPTII-activity (kanamycin resistance), grown to maturity and allowed to self-pollenate and set seed.

For phytase activity assays of the leaves of the transgenic plants, a segment of approx. 5 mm in diameter from a young leaf is taken from each plant, and homogenized in 300 μl 25 mM sodium-acetate buffer pH 5.5. Subsequently, phytase assays were carried out as described for the transient assays. In 32 independently transformed tobacco plants tested, a maximum activity was observed of 2 PTU/mg total soluble protein in the extracts. This corresponds to 1.7% of total soluble protein. In the seeds of these transformed tobacco plants, a maximum phytase expression level of 0.4% of the total soluble seed protein was observed. No phytase activity could be detected in untransformed plants.

Two transgenic plant lines, 413.25 and 413.32, were selected on the basis of their high expression levels of phytase.

Example 7

Cloning of the Phytase cDNA of *Aspergillus ficuum* in a Seed-specific Expression Construct An expression construct is constructed in such a way that seed-specific expression is obtained, using sequences of the *Brassica nanus* 12S storage protein gene cruciferin (cruA; Ryan et al., supra). These sequences may be replaced by those from similar seed-specific genes to achieve the same goal as is the objective of this invention.

The phytase cDNA is cloned into the expression construct. Finally, the entire construct is introduced into *Agrobacterium tumefaciens*, which is used for transformation.

For all *E. coli* transformations in this example, *E. coli* K-12 strain DH5α is used.

a) Construction of the expression construct

For the construction of the expression construct for seed-specific expression, the promoter and terminator sequences from the cruciferin A (cruA) gene of *Brassica napus* cv. Jet Neuf are synthesized using PCR technology with isolated genomic DNA (Mettler, I. J. (1987) Plant Mol. Biol. Rep. 5, 346) as a template. This gene shows seed-specific expression and its coding and flanking sequences have been determined (Ryan et al., supra).

Two sets of oligonucleotides are synthesized. One to allow amplification of the cruA 5' flanking region and part of the signal peptide encoding sequence as an EcoRI/NcoI fragment:

5' GTTCGGAATTCGGGTTCCGG 3' and 5' AACTGT-TGAGCTGTAGAGCC 3'.

The other for amplification of the 3' flanking sequence as a BglII/HindIII fragment:

5' CTTAAGATCTTACCCAGTGA 3' and 5' CGGAGAAGCTTGCATCTCGT 3'.

The oligo's are designed to contain suitable restriction sites at their termini to allow direct assembly of the expression construct after digestion of the fragments with the restriction enzymes.

The 5' fragment of the cruA gene, that includes 54 nucleotides of the sequence encoding the signal peptide is cloned into vector pMOG445 (Oligonucleotide duplex E (FIG. 4) cloned into vector pUC18, linearized with SstI and EcoRI), cut with EcoRI and NcoI, resulting in vector pMOG424. The synthetic oligonucleotide duplex D (FIG. 4), comprising the final 5 coding triplets for the signal sequence of Brassica napus cruciferin, the sequence encoding amino acids 1–6 of mature phytase and a multiple cloning site, is cloned in vector pMOG424 cut with NcoI and HindIII. The resulting vector is called pMOG425. The 3' cruA PCR fragment is cloned as a BglII/HindIII fragment into pMOG425 digested with BglII and HindIII, resulting in pMOG426.

b) Cloning of the phytase gene from Aspergillus ficuum in the binary vector

Plasmid pGB927, which contains the full-length coding sequence for Aspergillus ficuum phytase, is digested with XhoI (partially) and with PstI. The XhoI/PstI fragment comprising the DNA sequences encoding mature phytase from amino acid 6 onward is cloned in vector pMOG426, cut with XhoI and PstI. From the resulting vector pMOG428, the entire construct, containing the chimeric phytase gene, is inserted as an EcoRI/HindIII fragment in the binary vector pMOG23 linearized with EcoRI and HindIII. The resulting binary vector pMOG429 is mobilized, in a triparental mating with the E. coli K-12 strain RK2013 (containing plasmid pRK2013) (Ditta et al., supra), into Agrobacterium strain LBA4404 (Hoekema et al., 1983, supra) that contains a plasmid with the virulence genes necessary for T-DNA tranfer to the plant.

Example 8

Stable Seed-specific Expression of Phytase in Tobacco Seeds Under the Control of a Cruciferin Promoter Agrobacterium strain LBA4404, containing the binary vector pMOG429 with the phytase cDNA under the control of the cruciferin promoter, is used for transformation experiments. Transformation of tobacco (Nicotiana tabacum SR1) is carried out using cocultivation of leaf discs according to the procedure of Horsch et al., supra. Transgenic plants are regenerated from shoots that grow on selection medium (100 mg/l kanamycin). Young plants are assayed for NPTII-activity (kanamycin resistance), grown to maturity and allowed to self-pollenate and set seed. Seeds from individual transformants are pooled and part of the seed sample is assayed for the presence of phytase. From clones with the highest expression levels, compared to untransformed control seeds, the remaining seeds are germinated on kanamycin (200 mg/L). From data on the resulting S2 seeds, seeds homozygous for NPTII (hence also for phytase) are selected and used for mass propagation of plants capable of producing the highest amounts of phytase. These can then be used, e.g. for digestion experiments.

To determine the phytase activity found in the transgenic seeds, about 50 mg seed is taken and homogenized with a pestle in an ice-cold mortar in 1 ml 25 mM sodium-acetate buffer pH 5.5. After centrifugation, the supernatant is assayed as described for the transient assays. In 55 independently transformed tobacco plants, a maximum phytase expression level of 0.15% of the total soluble seed protein was observed. Phytase activity was not detected in stems, roots and leaves of the transgenic plants. No phytase activity could be detected in untransformed plants.

Example 9

Transformation of Rapeseed

In this example, the transformation of rapeseed by co-cultivation of plant tissue with Agrobacterium tumefaciens, containing a binary vector with the chimeric phytase gene is described. Transgenic plants may be selected on antibiotic resistance. The transgenic plants may be assayed for phytase activity. High expressors may be analyzed more thoroughly and used in further experiments.

The same chimeric phytase construct in a binary vector (pMOG429) is mobilized into Agrobacterium tumefaciens strain LBA4404, in a like manner as described in Example 7. This strain may be used to transform rapeseed (Brassica napus cv. Westar). To this aim, surface-sterilized stem segments taken from 5 to 6 week-old plants, just before flowering, are preconditioned for 24 h on MS medium (Fry at al. (1987) Plant Cell Reports 6, 321) with 1 mg/l BAP and then co-cultivated for 48 h with Agrobacterium on fresh plates with the same medium. Transgenic plantlets were regenerated from shoots that grow on selection medium (500 mg/l carbenicilline, 40 mg/l paromomycin) and further analyzed as described in Example 8 for tobacco.

Example 10

Phytase Activity Assay

An amount of transgenic plant material was ground which in total contain approximately 0.25 PTU. (PTU=Phytase units. One unit of phytase activity is defined as that amount of enzyme which liberates inorganic phosphorus from 1.5 mM sodium phytate at the rate of 1 $\mu$mol/min at 37° C. and at pH 2.5). Alternatively, this amount of phytase may be extracted from the plant material.

The ground plant material was incubated in a total volume of 50 ml of a 250 mM glycine/HCl buffer pH 2.5 containing 0.86 g sodium phytate.11 $H_2O$. Although Aspergillus phytase expresses a pH optimum at 2.5 as well as at 5.5, the lower pH is chosen to exclude plant phytase activity.

The resulting mixture is incubated for 15 and 60 minutes at 37° C. The reaction is stopped by the addition of 5 ml from the incubate into 5 ml of 10% TCA (trichloroacetic acid). Thereafter, 10 ml of indicator reagent (3.66 g of $FeSO_2.7H_2O$ in 50 ml of ammonium molybdate solution (2.5 g $(NH_4)6Mo_7O_{24}H_2O$ and 8 ml conc. $H_2SO_4$, diluted up to 250 ml with demiwater) is added to the stopped enzyme solution. The intensity of the blue color is measured spectrophotometrically at 700 nm.

The inorganic phosphate content present at T=0 serves as a blank.

The measurements are indicative of the quantity of phosphate released in relation to a calibration curve of phosphate in the range of 0–1 mM.

Example 11

Incubation of Around Nicotiana tabacum Plant Material with Feedstuffs

In a typical experiment, 0.25 g of solvent extracted soybean meal is incubated with a quantity of ground Nicotiana tabacum plant material containing approximately 0.25 PTU as described above, except for the addition of sodium phytate. In this case, the added incubation agent consists of a mixture of 410 ml buffer and 90 ml of demiwater.

Figure 6:
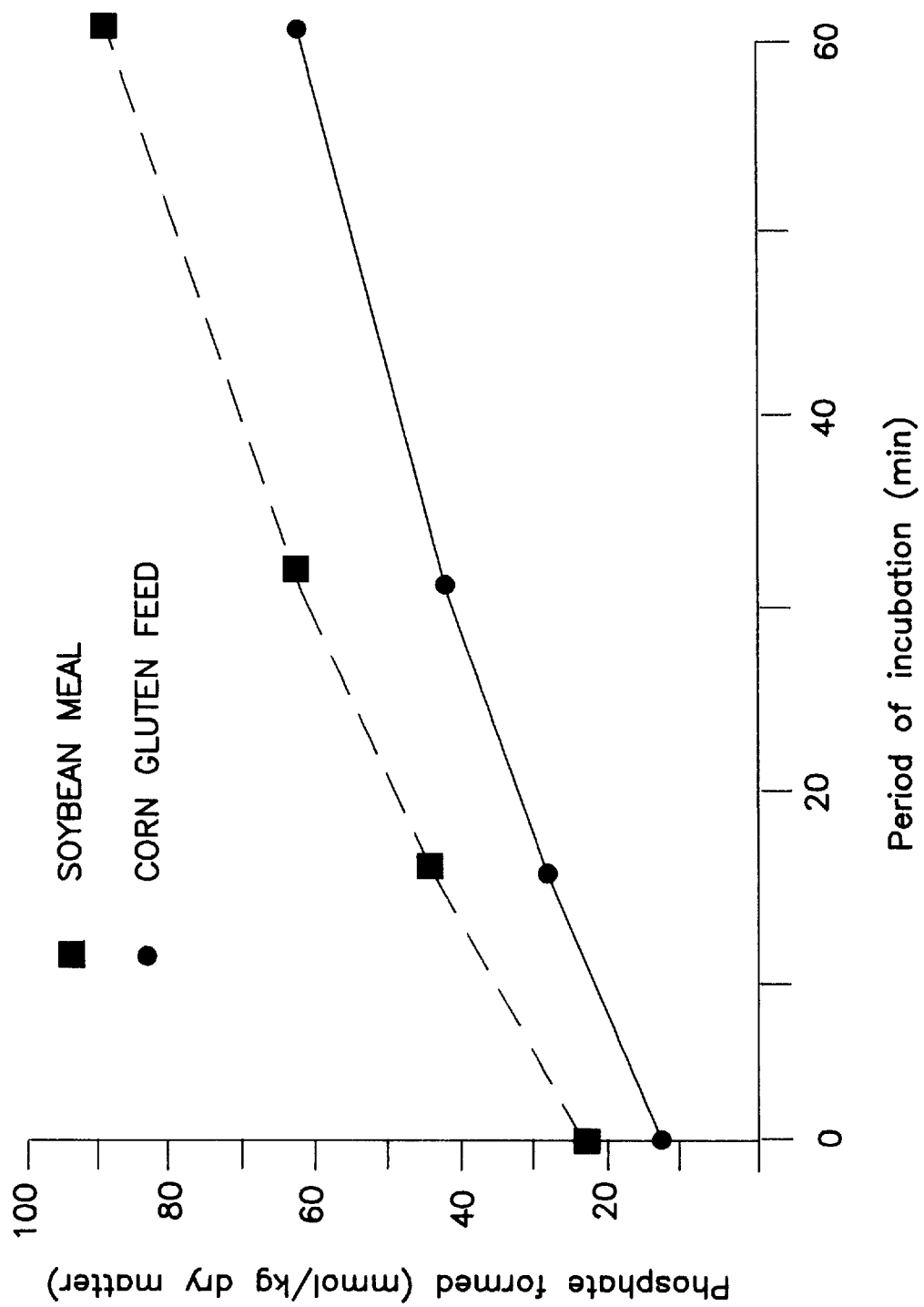
FIG. 6 is a graph showing the effects of the addition of ground seeds containing phytase on the liberation of inorganic phosphorous from phytate.

The liberation of phosphate from phytate in solvent extracted soybean meal is depicted in FIG. 6. Without added ground plant material, no activity is observed.

In a virtually identical experiment, similar results are obtained using maize gluten feed as a substrate. Results using transgenic seeds are shown in FIG. 6.

No activity is observed in the absence of ground plant material or when ground plant material are added which do not contain phytase activity.

Example 12

In vitro Testing of Transgenic Plant Material Containing Phytase Under Conditions Simulating the Digestive Tract of Poultry To assess the effectivity of phytase produced in transgenic tobacco plant material, the activity of phytase from Aspergillus is determined in a model simulating the conditions found in the digestive tract in poultry.

A standard poultry feed sample is first incubated at 1 g/15 ml demi water for 60 minutes at 39° C. to simulate the conditions in the crop of the animals. Subsequently, 5 ml of a pepsin solution (Merck: 5.28 g/l, pH 3.0-adjusted with HCl) is added, the pH adjusted with HCl to pH 3.0, and the incubation is continued for a further 90 minutes at the same temperature to simulate the conditions in the stomach.

During the incubation period, samples were taken in order to determine the amount of phosphate released from the phytate present in the feed.

Figure 7:
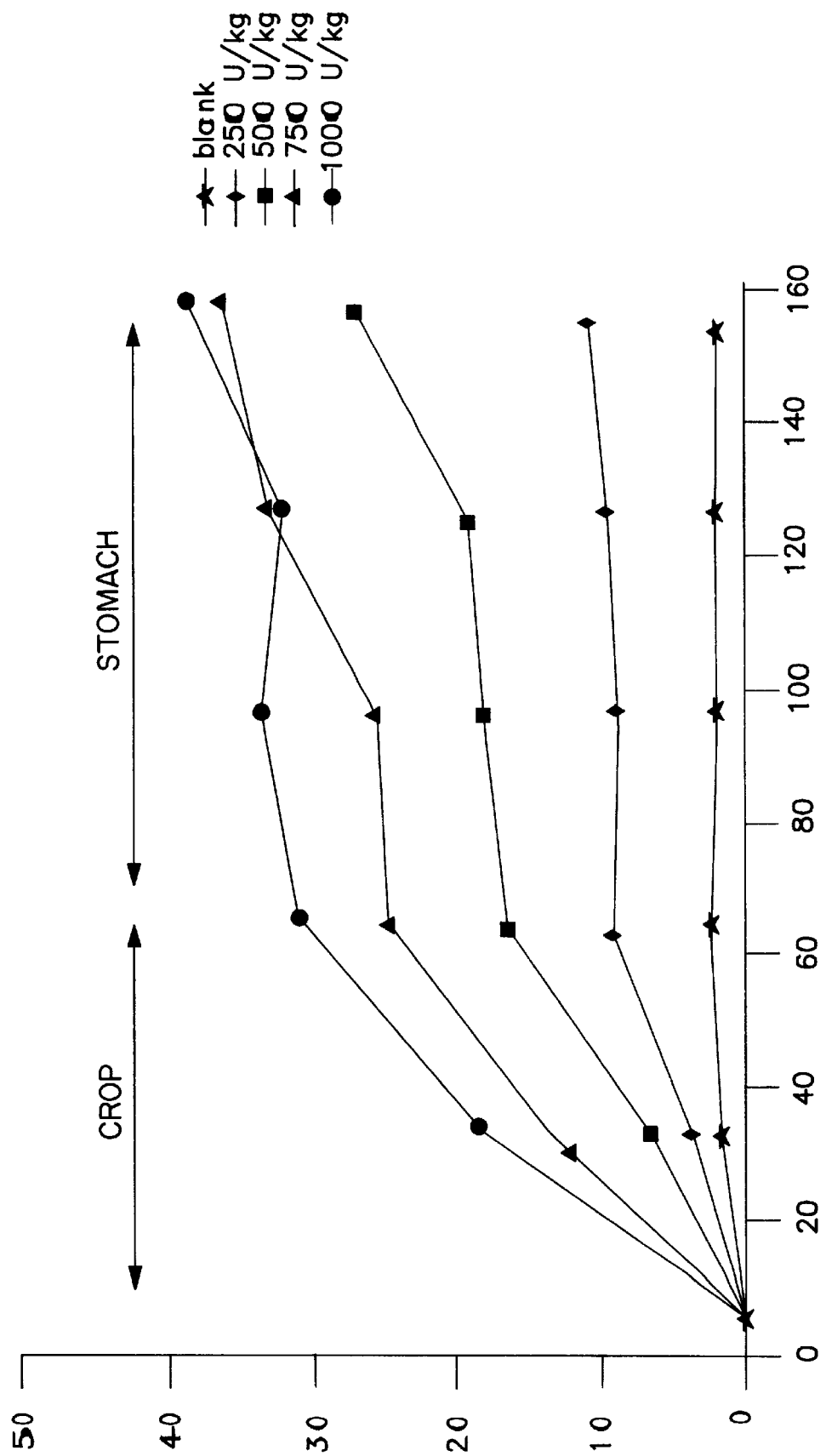
FIG. 7 is a graph showing dose-response relationship of Aspergillus phytase in an in vitro digestion model.

The action of fungal phytase is apparent from FIG. 7. Increasing the phytase dosage from 250 to 1000 PTU/kg feed results in an increased release of phosphate from the feed sample.

Figure 8:
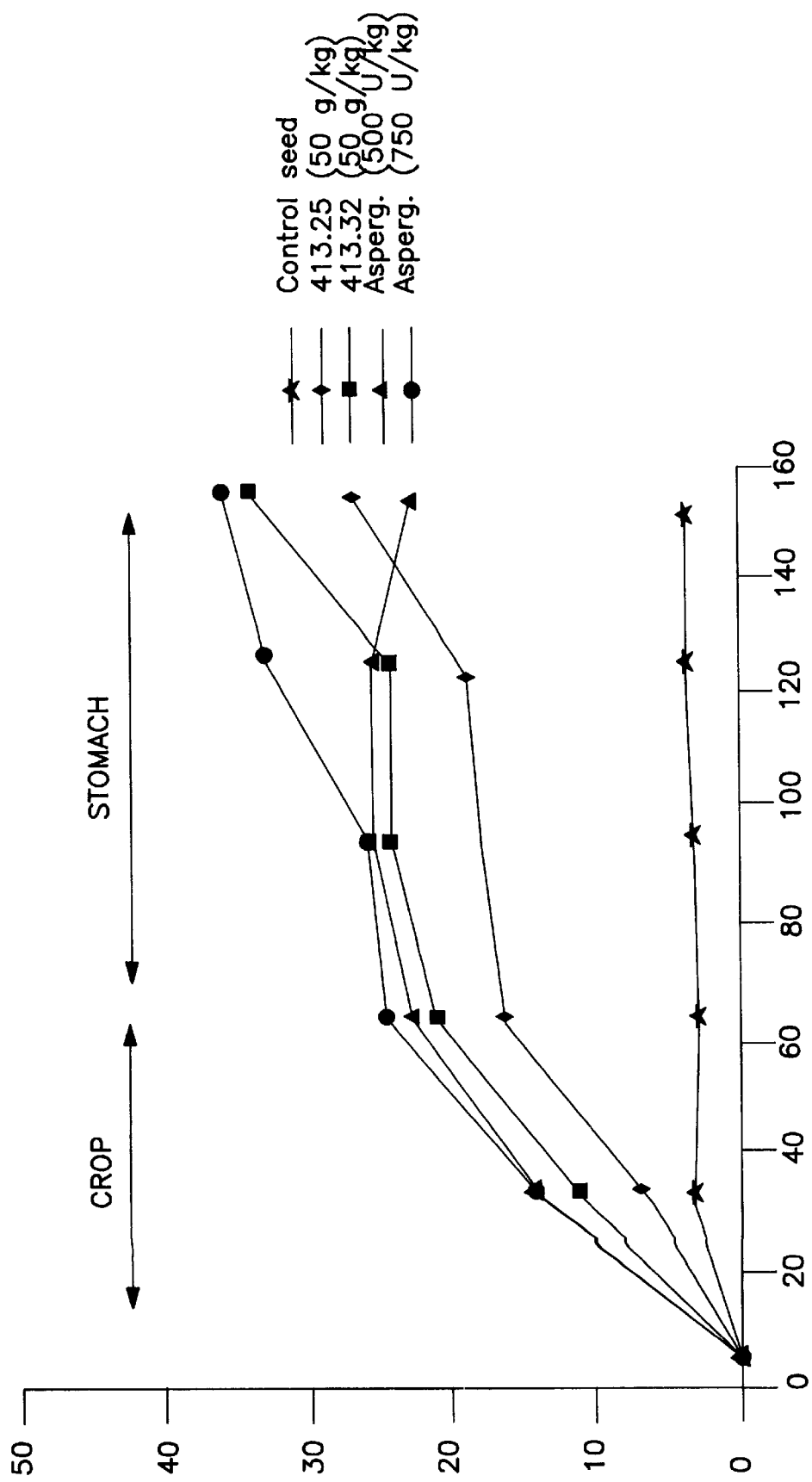
FIG. 8 is a graph showing dose-response relationship of Aspergillus phytase and phytase contained in tobacco seed in an of vitro digestion model.

When a sample of transgenic tobacco plant material, either seed or leaf (lines 413.25 and 413.32; after grinding in a mortar), is added in place of the fungal phytase, a similar increased phosphate release is observed (FIG. 8). Control tobacco plant material, which did not contain phytase, was also tested. No phosphate release was observed as compared to the blank control.

Comparison of the results with 50 g transgenic tobacco seed/kg feed with those obtained with 500 and 750 PTU/kg feed indicates that 1 g tobacco seed equals approximately 12 PTU in this in vitro poultry digestion model. A sample comparison using leaf material indicates that 1 g (fresh weight) of tobacco leaf material contains approximately 25 PTU.

Example 13

Animal Testing

Trials are carried out with broilers to show the efficacy of phytase expressed in plant seeds, as well as the absence of any negative effect of seeds from tobacco on zootechnical results.

Both phytase-expressing and control tobacco seed are harvested. Seeds were ground in 100 gram portions with a sieve (Retch-mill ZM1) having pores of 500 μm, taking care to keep the seeds cooled.

One day old male broiler chicks (Hybro) are housed in two tier battery cages (0.45 m²). The ambient temperature is 32° C. during the first two days and is decreased by 4° C. in the first week. Every following week, the temperature is decreased by 2° C. Broilers are reared in a one hour light and three hours dark regime.

The birds are vaccinated against New Castle Disease at one day of age using Clone 30 vaccine. During the experiments, the broilers are fed the experimental diets all mash and ad libitum. Growth and feed/gain ratios are measured during the experimental periods. Apparent availability of total phosphorus is measured in a three day period, during which feed consumption is measured as dry matter intake and excreta are collected quantitatively.

Apparent availability of phosphorus is defined as the difference between intake of phosphorus and excretion of phosphorus with the excreta.

The following control diets without addition of phytase are used:

| Diets | Ca (%) | total P (%) | phytate P (%) |
| --- | --- | --- | --- |
| 1 | 0.60 | 0.45 | 0.30 |
| 2 | 0.75 | 0.60 | 0.30 |
| 3 | 0.90 | 0.75 | 0.30 |

No graded feed phosphate is added to diet 1 (basal diet). Calcium and phosphorus from a mixture of anhydrous dicalcium phosphate and monoammonium phosphate (ratio 5:1) are supplemented to diets 2 and 3. All experimental diets are obtained by additions to the basal diet (see Table 1).

Experimental diet 4 contains microbial phytase at a concentration of 400 PTU/kg feed, prepared as described by Van Gorcom et al., supra.

Experimental diet 5 is like diet 4 but ground seeds of non-transgenic tobacco are added to the feed mixture to achieve a final ratio of 3 kg/90 kg feed.

Experimental diet 6 is also like diet 4 but 3 kg ground seeds of transgenic tobacco (line 413.25) are added to a mixture of 90 kg feed to obtain a final concentration of 400 PTU/kg feed.

The experiment is carried out with 176 broilers in 16 battery cages (11 per battery cage) until the age of 24 days. The treatments (diets) are repeated twice and are assigned randomly to the cages within each tier.

The availability of phosphorus is measured from 21–24 days of age.

The results with regard to phosphorous availability and growth of the animals supplied with diets 4, 5 and 6 each show the positive effect of the addition of phytase (Table 2). A comparison of diets 4, 5 and 6 also demonstrates that the inclusion of tobacco seeds in feed is compatible with the action of microbial phytase in the gastrointestinal tract of farm animals such as broilers and shows no negative effect on the zootechnical results.

Example 14

Storage Stability of Phytase Produced in Tobacco Seeds

The storage stability of phytase produced in tobacco seeds were determined at various time intervals and at different storage temperatures.

Figure 9:
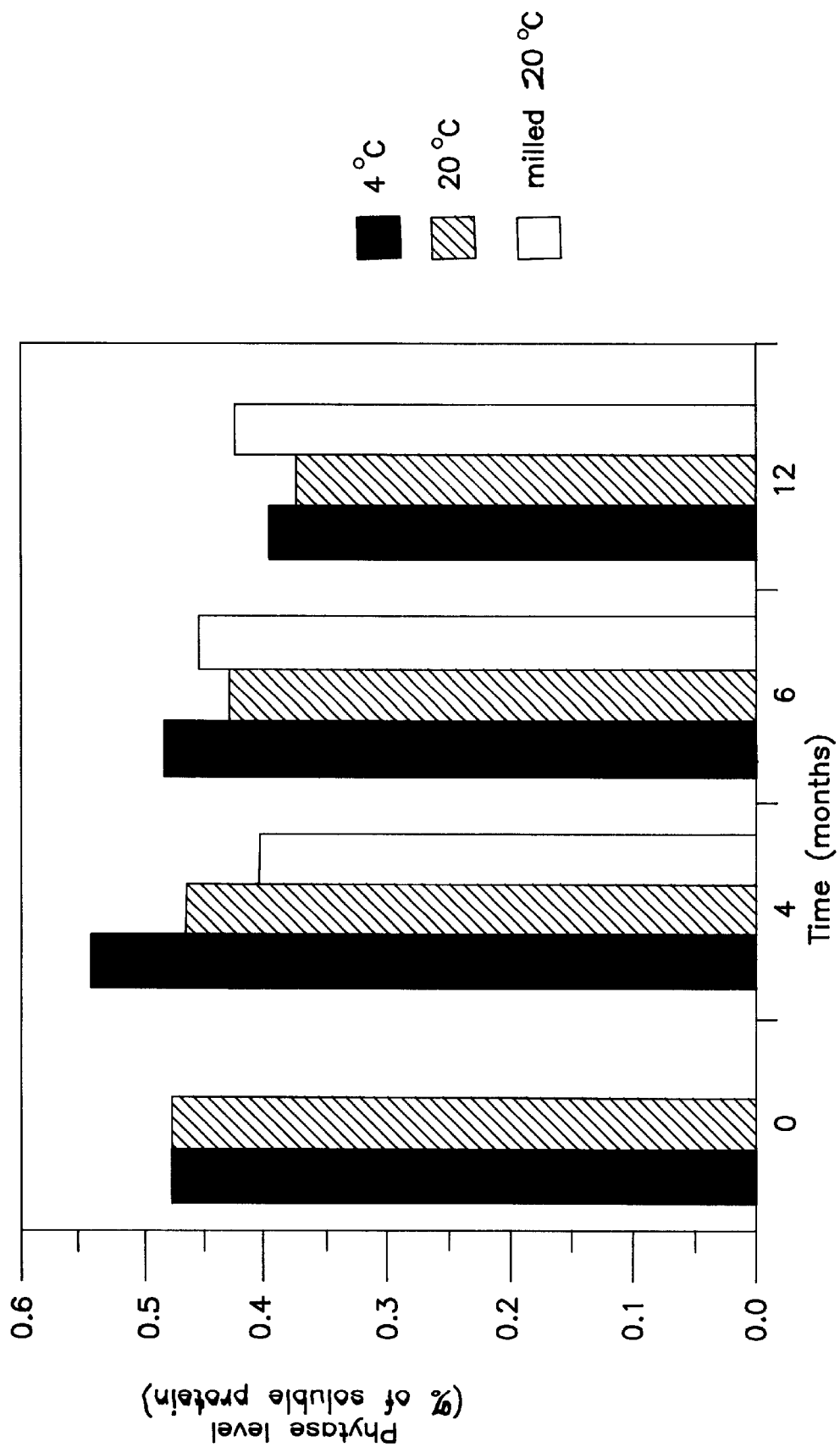
FIG. 9 is a histogram showing the storage stability of phytase produced in tobacco seeds.

Tobacco seeds of Nicotiana tabacum SR1 which has been transformed with the plasmid pMOG413 (see Example 6), in which phytase from *Aspergillus ficuum* was expressed extracellularly were stored at 4° C. and 20° C. Milled seeds were stored at 20° C. Phytase activity was determined at several time points. The enzyme appeared to be stable in whole, as well as in milled seeds (FIG. 9).

Example 15

Expression of Phytase Under Control of the ACP Promoter a) Isolation of a 0.6 kb BamHI/HindIII fragment comprising the terminator sequences from the *Agrobacterium tumefaciens* nopalin synthase (NOS) and the CaMV 35S genes The oligonucleotide duplex TCV11/12 was cloned in the HindIII site of pMOG29 (see Example 4). TCV11/12:

```
5' AGCTCTGCAGTGAGGTACCA3'

3'     GACGTCACTCCATGGTTCGA5'
```

The orientation of the adaptor TCV11/12 was checked by sequencing. A vector was used having the adaptor TCV11/12 in an orientation that would allow the cloning of the CaMV 35S terminator in a reverse orientation with respect to the *Agrobacterium tumefaciens* nopalin synthase (NOS) terminator sequence. In the resulting vector, linearized with PstI and KpnI, the 0.25 kb PstI/KpnI 35S terminator fragment isolated from plasmid pRT102 (Töpfer et al. (1987) Nucl. Acids Res. 15, 5890) was cloned. To destroy the PstI site, the obtained vector was linearized with PstI, blunted with Klenow polymerase, ligated and transformed to *E. coli*. From the resulting vector an 0.6 kb BamHI/HindIII fragment was isolated containing the terminator sequences from the *Agrobacterium tumefaciens* nopalin synthase (NOS) and the CaMV 35S genes, with the 35S terminator present in the reverse orientation.

b) Cloning and transformation of the binary vector

A 1 kb promoter of the seed-specific acyl carrier protein (ACP) gene from *Brassica napus* cv. Westar was synthesized by PCR as an EcoRI/NcoI fragment with isolated genomic DNA (Mettler, supra) as a template. Synthetic DNA primers ACPI and ACPII, based on the sequence published by de Silva, J. et al. ((1992) Plant Mol. Biol. 18, 1163–1172) were used in the PCR reaction.

```
ACPI   5' CGCGAATTCTGCAGCCAGAAGGATAAAG3'

ACPII  5' GTGGTCGCCATGGTCGATATTCACG3'
```

The EcoRI/NcoI fragment was cloned in pUC18, linearized with EcoRI and BamHI in a three-way ligation with the oligonucleotide duplex Trans1/2, encoding the signal peptide of the tobacco PR-S protein. Trans1/2:

```
5' CATGAACTTCCTCAAGAGCTTCCCCTTTTATGCCTTCCTTTGTTTTG

3'     TTGAAGGAGTTCTCGAAGGGGAAAATACGGAAGGAAACAAAA

GCCAATACTTTGTAGCTGTTACGCATGCTCGAG3'

CCGGTTATGAAACATCGACAATGCGTACGAGCTCCTAG5'
```

Figure 10:
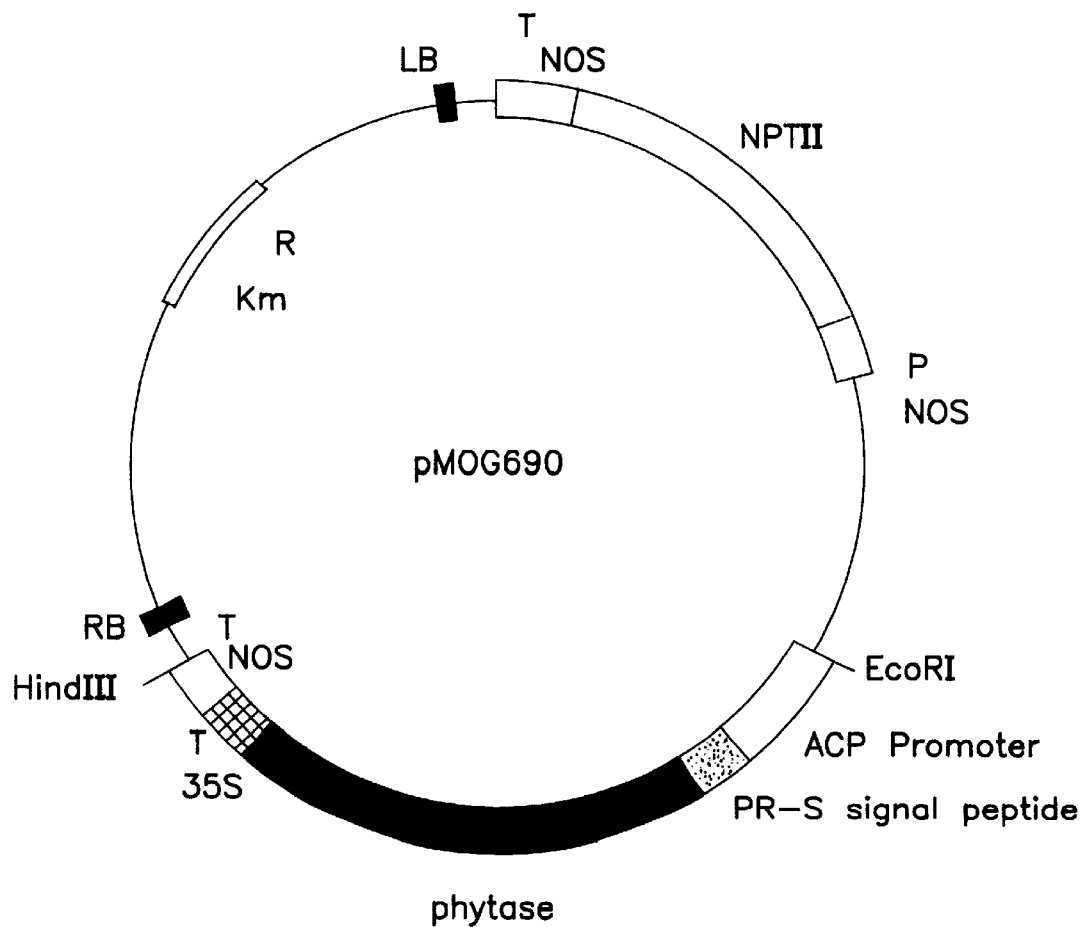
FIG. 10 is a diagram of plasmid pMOG690. Binary vector containing the phytase gene under control of the ACP promoter.

In the resulting vector, cut with SphI and BamHI, the phytase encoding cDNA fragment, isolated from pMOG417 (see Example 4) by digestion with SphI and BamHI (partial), was cloned. In this vector, linearized with BamHI (partial) and HindIII, an 0.6 kb DNA fragment containing the terminator sequences from the *Agrobacterium tumefaciens* nopalin synthase (NOS) and the CaMV 35S genes (with the 35S terminator present in the reverse orientation) was cloned. From the resulting vector, the 3.2 kb EcoRI/HindIII expression cassette was cloned into binary vector pMOG402 cut with EcoRI and HindIII. The resulting binary plasmid, designated pMOG690 (FIG. 10), was mobilized in a triparental mating with the *E. coli* strain HB101 containing plasmid pRK2013 (Ditta et al., supra), into Agrobacterium strain MOG101, which contains a plasmid having the virulence genes necessary for-T-DNA transfer to the plant (Hoekema et al., 1983, supra). Tobacco was transformed as described in Example 6. Transgenic seeds were harvested and assayed for phytase activity as described (see Example 10). The average expression level was 0.03% of soluble protein for 6 plants tested.

Example 16

Expression of Phytase Under Control of a 3 kb Cruciferin Promoter

A 3 kb promoter fragment of a cruciferin gene of *Brassica nanus* cv. Jet Neuf was used to control the expression of the phytase gene. The promoter fragment was fused to a DNA fragment encoding the AMV RNA4 leader, the tobacco PR-S signal peptide, mature phytase and the terminator sequences from the Agrobacterium nopalin synthase (NOS) and the CaMV 35S genes.

Isolated genomic DNA of *Brassica napus* cv. Jet Neuf was digested with SalI and BamHI, run on an agarose gel, blotted and hybridized with the PCR fragment comprising the 5' flanking region of the cruciferin A (cruA) gene (see Example 7). Southern hybridization showed a strongly hybridizing fragment of about 2.8 kb. *Brassica nanus* cv. Jet Neuf DNA, digested with SalI and BamHI was size-fractionated on a 10%–20% sucrose gradient. The fraction containing DNA fragments of approximately 2.5–3.2 kb was ligated in plasmid pGEM4 (Promega), linearized with SalI and BamHI. This ligation was transformed to *E. coli* strain DH10 (Gibco BRL), resulting in a partial genomic DNA library of about 100,000 clones. This library was screened with the PCR fragment of the cruA gene (see above) as a probe. One positive clone, designated pMOGcru, was found to contain a fragment that in the corresponding part was more than 95% identical with the cruA promoter sequence published by Ryan et al. (supra).

A set of synthetic oligonucleotides, TCV9 and TCV10 were used to synthesize by PCR technology a fragment consisting of the distal 13 bp of the cruA promoter from the PvuII site to the RNA start site followed by the RNA4 leader sequence of alfalfa mosaic virus (AMV) and the signal peptide-encoding sequence of the tobacco PR-S protein using plasmid pMOG417 (see Example 4) as a template.

```
TCV9
5' CAGAGCATGCGTAACAGCTAC                      3'

TCV10
5' CGGAATTCGGCAGCTGTAAGACCAGAGGGTTTTTATTTTTA 3'
```

The thus-obtained 123 bp PCR fragment was cloned in a pGEM4 vector lacking the PvuII site (The PvuII site was destroyed by, in sequence, overdigestion of pGEM4 with PvuII, ligation, digestion with PvuII, transformation to *E. coli*, and screening for clones lacking the PvuII site), linearized with EcoRI and PvuII. The resulting vector was linearized with EcoRI and PvuII, and used in a three-way ligation containing additionally a 0.1 kb SalI/PvuII cruA promoter fragment from plasmid pMOG428 (see Example 7) and the 2.8 kb EcoRI/SalI cruciferin promoter fragment from pMOGcru (see above). In the obtained vector, cut with SphI and BamHI, the 1.5 kb cDNA fragment from pMOG417 encoding phytase (see Example 4), obtained by digestion with SphI and BamHI (partial), was cloned. In the resulting vector, linearized with BamHI (partial) and HindIII, an 0.6 kb DNA fragment consisting of the terminator sequences from the Agrobacterium nopalin synthase (NOS) and the CaMV 35S genes was cloned. The CaMV 35S terminator was present in the reverse orientation (see Example 15). The 5.2 kb expression cassette was cut out with EcoRI and HindIII (partial), and cloned into binary vector pMOG402 cut with EcoRI and HindIII.

Figure 11:
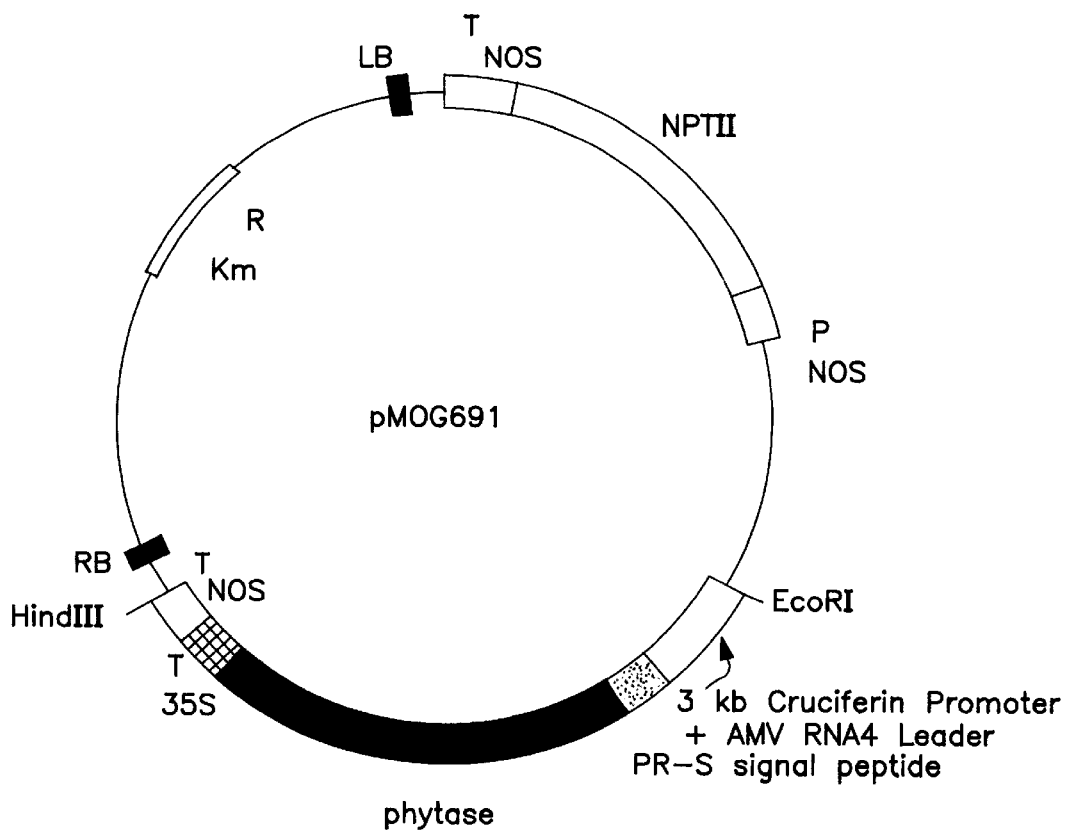
FIG. 11 is a diagram of plasmid pMOG691 containing the phytase gene under control of a 3 kb cruciferin promoter.

The resulting binary plasmid, designated pMOG691 (FIG. 11), was mobilized in a triparental mating with the E. coli strain HB101 containing plasmid pRK2013 (Ditta et al., 1980), into Agrobacterium strain MOG101, which contains a plasmid having the virulence genes necessary for T-DNA transfer to the plant (Hoekema et al., 1983). Tobacco was transformed as described in Example 6. Transgenic seeds were harvested and assayed for phytase activity as described (see Example 10). The average expression level was 0.3% of soluble protein for 9 plants tested.

While the present invention has been described with reference to specific embodiments thereof, it should be understood by those skilled in the art that various changes may be made and equivalents may be substituted without parting from the true spirit and scope of the invention. In addition, many modifications may be made to adapt a particular situation, material, plant, seed, process, process step or steps to the object, spirit and scope of the invention. All such modifications are intended to be within the scope of the claims appended hereto.

TABLE 1

Composition of basal diet in experiments with broilers

| Ingredients | Contents (g/kg) |
| --- | --- |
| Yellow maize | 280.0 |
| Sorghum (low tannin) | 200.0 |
| Sunflower seed meal (solv. extr.) | 80.0 |
| Soya bean meal (solvent extr., 48.8% protein) | 350.0 |
| Soya bean oil | 58.5 |
| Vitamins* | 5.0 |
| Minerals* | 15.0 |
| Limestone | 1.0 |
| Synth. methionine | 1.0 |
| $Cr_2O_3$ | 0.5 |
| | 1001.0 |
| ME (MJ/kg) | 13.1 |
| Lysine | 12.9 |
| Methionine + cystine | 9.1 |
| Calcium | 6.0 (6.0–6.6)** |
| Total phosphorus | 4.5 (4.7–4.7)** |
| Organic phytic phosporus | 3.0 (3.1–3.1)** |

*Amount supplied per kg diet: 12000 IU vitamin A; 2000 IU vitamin $D_3$; 5 IU vitamin E; 1.5 mg vitamin $K_3$; 1 mg thiamine; 5 mg riboflavin; 1 mg pyridoxine; 30 mg nicotinic acid, 7.5 mg D-pantothenic acid; 0.015 mg vitamin $B_{12}$; 0.5 mg folic acid; 350 mg choline chloride; 75 mg ethoxyquin; 9.5 g $CaCo_3$; 2.5 g NaCl; 0.26 g $FeSO_4$; 0.24 g $MnSO_4$; 45 mg $CuSO_4$; 60 mg $ZnSO_4$; 105 mg KI mixture.
**( ) Analyzed for experiments 1 and 2 respectively.

TABLE 2

Effect of Phytase on the Apparent Availability of Total P and Ca, the P Content in Manure and the Performance of Broilers

| Diets | Ca/P (g/kg) | Added phytase (units/ kg) | Availability (%) 21–24 d | | Amount of P in manure (g) per kg dm | Growth 0–24 d |
| --- | --- | --- | --- | --- | --- | --- |
| | | | P | Ca | feed intake | (g) |
| 1 | 6/4.5 | 0 | 49.8 | 47.2 | 2.7 | 338 |
| 2 | 7.5/6 | 0 | 45.6 | 48.9 | 3.8 | 592 |
| 3 | 9/7.5 | 0 | 44.6 | 46.9 | 4.9 | 683 |
| 4 | as 1 | 400 | 60.5 | 58.6 | 2.1 | 620 |
| 5 | as 1 | 0 | 48.5 | 48.0 | 2.7 | 340 |
| 6 | as 1 | 400 | 60.2 | 59.3 | 2.1 | 615 |

We claim:

1. A feed composition for animals which comprises a phytase recombinantly produced in plants, wherein said phytase is recombinantly produced by a method which comprises
    providing an expression construct which contains a nucleotide sequence encoding a phytase operably linked to regulatory sequences that direct the expression of the nucleotide sequence encoding phytase in a plant cell;
    stably transforming a plant cell, plant part or plant with the expression construct;
    culturing the plant cell, plant part or plant under conditions wherein the phytase-encoding nucleotide sequence is expressed; and
    processing the plant cell, plant part or plant under conditions appropriate for use of said phytase in an animal feed composition.

2. The composition of claim 1 wherein the phytase is of a plant source.

3. The composition of claim 1 wherein said phytase has been recovered and purified from said plant cell, plant part or plant.

4. The composition of claim 1 wherein the phytase catalyzes the liberation of inorganic phosphate from myo-inositol hexakis-phosphate.

5. The composition of claim 1 wherein the step of processing the plant cell, plant part or plant comprises the additional step of grinding said plant cells, plant parts or plants.

6. The composition of claim 1 wherein the step of processing said plant cell, plant part or plant comprises the additional step of combining said plant cells, plant parts or plants with other components appropriate in a composition for hydrolysis of phytate.

7. A method to promote the growth of an animal and reduce the level of phytate in the feces of said animal, which method comprises feeding said animal the feed composition of claim 1.

* * * * *